US008771500B2

(12) United States Patent
Papadimitrakopoulos et al.

(10) Patent No.: US 8,771,500 B2
(45) Date of Patent: Jul. 8, 2014

(54) GLUCOSE SENSORS AND METHODS OF MANUFACTURE THEREOF

(75) Inventors: Fotios Papadimitrakopoulos, West Hartford, CT (US); Santhisagar Vaddiraju, Willimantic, CT (US)

(73) Assignee: The University of Connecticut, Farmington, CT (US)

( * ) Notice: Subject to any disclaimer, the term of this patent is extended or adjusted under 35 U.S.C. 154(b) by 1077 days.

(21) Appl. No.: 12/256,043

(22) Filed: Oct. 22, 2008

(65) Prior Publication Data

US 2009/0101498 A1  Apr. 23, 2009

Related U.S. Application Data

(60) Provisional application No. 60/999,914, filed on Oct. 22, 2007.

(51) Int. Cl.
*C12Q 1/00* (2006.01)
*G01N 27/26* (2006.01)
*G01N 33/50* (2006.01)
*G01F 1/64* (2006.01)

(52) U.S. Cl.
USPC ........ 205/777.5; 205/775; 205/778; 205/792; 205/793; 204/403.01; 204/403.04; 204/403.05; 204/403.06; 204/403.1; 204/403.14; 600/347

(58) Field of Classification Search
USPC ........ 600/309, 345–366; 204/403.01–403.15; 205/775, 777.5, 778, 792, 793
See application file for complete search history.

(56) References Cited

U.S. PATENT DOCUMENTS

| 4,484,987 | A | 11/1984 | Gough |
| 5,030,333 | A | 7/1991 | Clark, Jr. |
| 2003/0099682 | A1 * | 5/2003 | Moussy et al. ............. 424/423 |
| 2007/0299617 | A1 * | 12/2007 | Willis ............................ 702/19 |

OTHER PUBLICATIONS

F. Moussy, D. J. Harrison, D. W. O'Brien and R. V. Rajotte, Performance of Subcutaneously Implanted Needle-Type Glucose Sensors Employing a Novel Trilayer Coating, Anal. Chem. 1993, 65, 2072-2077.*
N. Wisniewski, F. Moussy, W.M Reichert, Characterization of implantable biosensor membrane biofouling, Fresenius J. Anal. Chem. (2000) 366:611-612 (2000).*
X. Liu, K. Nakamura, and A. M. Lowman, Composite Hydrogels for Sustained Release of Therapeutic Agents, Soft Material, vol. 1, No. 3, pp. 393-408 (2003).*

(Continued)

*Primary Examiner* — Luan Van
*Assistant Examiner* — Maris R Kessel
(74) *Attorney, Agent, or Firm* — Cantor Colburn LLP

(57) ABSTRACT

Disclosed herein is a device that functions as a glucose sensor. The device has a reference electrode; a counter electrode, a working electrode; an electrically conducting membrane; an enzyme layer; a semi-permeable membrane; a first layer of a first hydrogel in operative communication with the working electrode; the first layer of the first hydrogel being operative to store oxygen; wherein the amount of stored oxygen is proportional to the number of freeze-thaw cycles that the hydrogel is subjected to; and a second layer of the second hydrogel. Disclosed too is a method that comprises using periodically biased amperometry towards interrogation of implantable glucose sensors to improve both sensor's sensitivity and linearity while at the same time enable internal calibration against sensor drifts that originate from changes in either electrode activity or membrane permeability as a result of fouling, calcification and/or fibrosis.

8 Claims, 16 Drawing Sheets

(56) References Cited

OTHER PUBLICATIONS

G. Nagy, et al., "A New Type of Enzyme Electrode: The Ascorbic Acid Eliminator Electrode", Life Sciences (1982) pp. 2611-2616; Pergamon Press Ltd.
M. Shichiri, et al., "Long-Term Application of Wearable Artificial Endocrine Pancreas Closed-Loop Intravenous vs Subcutaneous Insulin Infusion"; Life Support Syst. (1985) pp. 583-587.
S.L. Jacques, et al. "Controlled Removal of Human Stratum Corneum by Pulsed Laser"; The Journal of Investigative Dermatology (1987) pp. 88-93; The Society for Investigative Dermatology, Inc.
G. G. Neuburger, et al., "Pulsed Amperometric Detection of Carbohydrates at Gold Electrodes with a Two-Step Potential Waveform"; Anal. Chem. (1987) pp. 150-154, vol. 59; American Chemical Society.
A. Heller "Electrical Connection of Enzyme Redox Centers to Electrodes"; J. Phys. Chem. (1992) pp. 3579-3587, vol. 96; American Chemical Society.
F. Moussy, et al. "Performance of Subcutaneously Implanted Needle-Type Glucose Sensors Employing a Novel Trilayer Coating"; Anal. Chem. (1993) pp. 2072-2077, vol. 65; American Chemical Society.
E. Katz, et al. "Electrical Contact of Redox Enzymes with Electrodes: Novel Approaches for Amperometric Biosensors"; Bioelectrochemistry and Bioenergetics (1997) pp. 95-104, vol. 42; Elsevier Science S.A.
S.B. Hall, et al., "Electrochemical Oxidation of Hydrogen Peroxide at Platinum Electrodes. Part 1. An Adsorption-Controlled Mechanism"; Electrochimica Acta (1997) pp. 579-588, vol. 43, Nos. 5-6; Elsevier Science Ltd. Great Britain.
B. Liu, et al. "Characterization of Immobilization of an Enzyme in a Modified Y Zeolite Matrix and Its Application to an Amperometric Glucose Biosensor"; Anal. Chem. (1997) pp. 2343-2348, vol. 69, No. 13; American Chemical Society.
R.C. Mercado, et al., "In Vitro and In Vivo Mineralization of Nafion Membrane Used for Implantable Glucose Sensors"; Biosensors & Bioelectronics (1998) pp. 133-145, vol. 13, No. 2; Elsevier Science S.A. Great Britain.
A.W. Bott, et al., "Electochemical Methods for the Determination of Glucose"; Current Separations (1998) pp. 25-31, vol. 17:1, Bioanalytical Systems, Inc.; Indiana, USA.
M. Gerritsen, et al., "Performance of Subcutaneously Implanted Glucose Sensors for Continuous Monitoring", The Netherlands' Journal of Medicine (1999) pp. 167-179, vol. 54, Elsevier Science B.V.
A. Heller, "Implanted Electrochemical Glucose Sensors for the Management of Diabetes", Annual Review Biomed. Eng. (1999) pp. 153-175, vol. 1, Annual Reviews.
A.P.F. Turner, et al., "In Vitro Diagnostics in Diabetes: Meeting the Challenge", Oak Ridge Conference; Clinical Chemistry (1999) pp. 1596-1601, vol. 45:9, Institute of BioScience and Technology, Cranfield University, UK.
J. Wang, et al., "Myoglobin-Containing Carbon-Paste Enzyme Microelectrodes for the Biosensing of Glucose Under Oxygen-Deficit Conditions", Analytical Chemistry (1999) pp. 5009-5011, vol. 71, No. 21, American Chemical Society.
G.S. Wilson, et al., "Enzyme-Based Biosensors for In Vivo Measurements", Chemical Reviews (2000) pp. 2693-2704, vol. 100, American Chemical Society.
J. Wang, et al., "Evaluation of Different Fluorocarbon Oils for Their Internal Oxygen Supply in Glucose Microsensors Operated Under Oxygen-Deficit Conditions".
H.L. Lutgers, et al., "Microdialysis Measurement of Glucose in Subcutaneous Adipose Tissue up to Three Weeks in Type 1 Diabetic Patients", The Netherlands' Journal of Medicine (2000) pp. 7-12, vol. 57, Elsevier Science B.V.
I. Galeska, et al., "Calcification-Resistant Nafion/Fe3+ Assemblies for Implantable Biosensors", Biomacromolecules (2000) p. Est: 5.9, American Chemical Society.

W. Kerner, "Implantable Glucose Sensors: Present Status and Future Developments", Experimental and Clinical Endocrinology and Diabetes (2001) pp. S341-S346, vol. 109, Suppl. 2, Johann Ambrosius Barth.
J. Wang, "Glucose Biosensor: 40 Years of Advances and Challenges", Electroanalysis (2001) pp. 983-988, vol. 13, No. 12, Wiley-VCH, Germany.
J. J. Burmeister, et al., "Self-Referencing Ceramic-Based Multisite Microelectrodes for the Detection and Elimination of Interferences from the Measurement of L-Glutamate and Other Analytes", Analytic Chemistry (Mar. 1, 2001) pp. 1037-1042, vol. 73, No. 5, American Chemical Society.
T. Koschinsky, et al., "Sensors for Glucose Monitoring: Technical and Clinical Aspects", Diabetes/Metabolism Research and Reviews (2001) pp. 113-123, vol. 17, John Wiley and Sons, Ltd.
I. Galeska, et al., "Characterization and Biocompatibility Studies of Novel Humic Acids Based Films as Membrane Material for an Implantable Glucose Sensor" Biomacromolecules (2001) pp. 1249-1255, vol. 2, American Chemical Society.
M. Rohrscheib, et al., "Non-Invasive Glucose Sensors and Improved Informatics—the Future of Diabetes Management" Biabetes, Obesity and Metabolism (2003) pp. 280-284, vol. 5, Blackwell Publishing, Ltd.
R.A. Jeong, et al., "In Vivo Calibration of the Subcutaneous Amperometric Glucose Sensors Using a Non-Enzyme Electrode" Biosensors and Bioelectronics (2003) pp. 313-319, vol. 19, Elsevier B.V.
Editorial: "Non-Invasive Photonic-Crystal Material for Sensing Glucose in Tears" Clinical Chemistry (2004) pp. 2236-2237, vol. 50, No. 12.
B. Leboulanger, et al. "Reverse Iontophoresis for Non-Invasive Transdermal Monitoring", Physiological Measurement (2004) pp. R35-R50, vol. 25, Institute of Physics Publishing (IOP Publishing, Ltd.) UK.
E.A. Moschou, et al., "Fluorescence Glucose Detection: Advances Toward the Ideal In Vivo Biosensor", Journal of Fluorescence (Sep. 2004) pp. 535-547, vol. 14, No. 5, Springer Science + Business Media, Inc.
G.S. Wilson, et al. "Biosensors for Real-Time In Vivo Measurements" Biosensors and Bioelectronics (2005) pp. 2388-2430, vol. 20, Elsevier B.V.
J.D. Newman, et al., "Home Blood Glucose Biosensors: A Commercial Perspective", Biosensors and Bioelectronics (2005) pp. 2435-2453, vol. 20, Elsevier B.V.
R. Gifford, et al., "Protein Interactions with Subcutaneously Implanted Biosensors", Biomaterials (2006), pp. 2587-2598, vol. 27, Elsevier, Ltd.
R. Tipnis, Etal., "Layer-by-Layer Assembled Semipermeable Membrane for Amperometric Glucose Sensors" Journal of Diabetes Science and Technology (Mar. 2007) pp. 193-200, vol. 1, Issue 2, Diabetes Technology Society.
S.M. Kirwan, et al. "Modifications of Poly (o-phenylenediamine) Permselective Layer on Pt-Ir for Biosensor Application in Neurochemical Monitoring", Sensors (2007) pp. 420-437, vol. 7, MDPI.
H.E. Koschwanez, et al. "In Vitro, In Vivo and Post Explantation Testing of Glucose-Detecting Biosensors: Current Methods and Recommendations", Biomaterials (2007) pp. 3687-3703, vol. 28, Elsevier, Ltd.
S. Vaddiraju, et al., "The Role of H2O2 Outer Diffusion on the Performance of Implantable Glucose Sensors", Biosensors and Bioelectronics (2008), 6 pages, Elsevier B.V.
Diabetes Monitor—diabetes on the web: devices for glucose monitoring, [online]; [Retrieved on Jan. 13, 2009]; retrieved from the internet. <http:// www.diabetesmonitor.com/other-3a.htm.
Kumetrix, Inc., [online]; [Retrieved on Jan. 13, 2009]; retrieved from the internet. <http://www.kumetrix.com.

* cited by examiner

GLUCOSE SENSORS AND METHODS OF MANUFACTURE THEREOF

STATEMENT OF FEDERAL SUPPORT

The present invention was developed in part with funding from the U.S. Army Research Office under Grant # W81XWH-05-1-0539. The United States Government has certain rights in this invention.

CROSS-REFERENCE TO RELATED APPLICATIONS

This application claims priority to provisional application 60/999,914 filed on Oct. 22, 2007, the entire contents of which are hereby incorporated by reference.

BACKGROUND

This disclosure relates to glucose sensors and to methods of manufacture thereof.

The control of Type I Diabetes Mellitus is generally effected by the periodic injection of insulin to maintain blood glucose levels as close to normal as possible. The blood glucose level is monitored by means of a device that directly measures glucose from a blood sample. Insulin is injected in the appropriate quantities and at the appropriate intervals to correct imbalances in the blood glucose level. Careful control of blood glucose levels is mandatory for preventing the onset of complications such as retinopathy, nephropathy and neuropathy. Unfortunately in many cases, patients neglect to perform regular glucose monitoring and therefore suffer episodes of hyperglycemia or hypoglycemia, which may, in turn, lead to the complications listed above or to death.

Blood-glucose levels generally vary with activity or food intake and insulin is therefore administered by sub-cutaneous hypodermic injection to minimize variations in the blood glucose levels that generally occur with activity or food intake. Small externally worn pumps are also available to deliver insulin percutaneously, thereby replacing the tedious use of a hypodermic injection, but constant glucose monitoring is still an important component of control.

Attempts to develop a closed loop system for the control of glucose levels have led to the development of ever more sophisticated insulin pump systems. However, an accurate long lived implanted blood glucose level monitor that would provide the desired signal for a closed loop insulin pump control is not yet available. An implanted blood glucose level monitor hinges on the accuracy of measuring glycemic levels in diabetic patients, thereby imposing stringent requirements in the confidence level of the continuous monitoring technology. In recent years, three kinds of glucose sensors are being developed: non-invasive, minimally-invasive and invasive.

Non-invasive techniques acquire spectroscopic information through skin or from various body fluids/gases (i.e., saliva, tears, and breath) and attempt to correlate this with glucose concentration. Non-invasive techniques generally use explanted sensors. Minimally-invasive sensors measure glucose concentrations from fluids obtained from the interstitial tissue of the skin via microdialysis, iontophoresis, laser ablation, and silicon-based micro-needle technologies. Both non- and minimally-invasive methods use elaborate calibration schemes and have considerable subject-to-subject variability.

Invasive methods use implanted sensors. These are generally advantageous in that they exhibit smaller subject-to-subject variability. However they are associated with a number of other problems. In particular, inflammation associated with tissue injury and the continuous presence of a foreign object is exacerbated by implant size and the presence of leads or fluid-microcatheters protruding through the skin. This constitutes the main cause of sensor failure in vivo, along with sensor element decays due to long-term usage.

Tissue injury-based sensor bio-instability is considered to be a result of the in vivo environment since explanted sensors often function normally without giving rise to any problems. It is generally believed that inflammation initiated fibrosis, calcification, and protein fouling are the leading causes of in vivo sensor failure. Implantation trauma, lack of biocompatibility of sensor materials and the physical presence of the sensor in the tissue are responsible for such tissue responses. Negative tissue responses (such as, biofouling, inflammation causing fibrosis and calcification) inhibit analyte migration and hence sensor performance; long-term sensor stability; and in vivo sensor calibration. Fibrous encapsulation can deprive the sensor of adequate blood and analyte supply. This can be modeled by effectively changing the permeability constants of the membrane(s) that surrounds the sensing element.

The D-glucose (dextrose monohydrate) specificity of analyte-specific enzymes such as glucose oxidase ($GO_x$), have helped propel Clark-type electrochemical detection as a major technological frontier in the development of implantable glucose sensors. The most commonly used glucose sensors are Clarke-type amperometric electrochemical sensors and are based on $GO_x$-catalyzed oxidation of glucose with $O_2$, shown in reaction (1). The principle of detection is based on the amperometric sensing of hydrogen peroxide ($H_2O_2$), formed by the oxidation of glucose. Under an applied potential of 0.7 V against a silver/silver chloride (Ag/AgCl) reference electrode, $H_2O_2$ is electrochemically oxidized according to reaction (2), and the current produced is related to the concentration of glucose in the system.

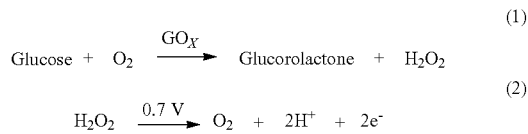

$$\text{Glucose} + O_2 \xrightarrow{GO_X} \text{Glucorolactone} + H_2O_2 \quad (1)$$

$$H_2O_2 \xrightarrow{0.7\,V} O_2 + 2H^+ + 2e^- \quad (2)$$

In testing methodology, the sensor is biased continuously at 0.7 V while the change in electrochemical response is measured, which in turn corresponds to the glucose levels. For the accurate performance of these sensors it is desirable that the amount of oxygen present within the sensor geometry must always be equal or higher than that of the glucose concentration. However, the dissolved oxygen concentration in ambient or in a biological fluid sample is significantly lesser than that of the glucose concentration, leading to an oxygen limiting reaction of the $GO_x$ enzyme. This results in a saturation of the electrochemically detected signal, making it impossible to determine higher levels of glucose in the blood. As a result of this saturation in the amperometric signal (defined as apparent Michael's constant $K_m^{app}$) any further increase in glucose concentration does not translate to adequate sensitivity.

This issue has been addressed by the use of diffusion limiting outer membranes. These membranes provide a greater impendence to the larger sized substrate (glucose) as opposed to the smaller sized co-substrate ($O_2$). For this, semipermeable membranes based on NAFION®, polyurethane, cellulose acetate, epoxy resins, polyether-polyethersulfone copolymer membranes, and layer by layer (LBL) assembled polyelectrolytes and/or multivalent cations have been extensively investigated. However, the use of semipermeable membranes comes at the expense of decreased sensitivity and increased sensor response time. Furthermore, the accumulation of exogenous reagents within these membranes (i.e., calcification, biofouling, or the like) leads to sensor drifts and their eventual failure.

In another variation, an additional oxygen reservoir can be incorporated into the outer membrane by incorporating oxygen-absorbing zeolites. Similarly, oxygen reservoirs such as fluorocarbon based oxygen reservoirs, mineral oils and myoglobin can be incorporated into the glucose oxidase enzyme layer.

In another variation, second- and third-generation Clark type biosensors employ redox mediators and direct 'wiring' of enzymes to electrodes in an attempt to minimize the effect of $O_2$. In the case of mediators, their toxicity and biocompatibility along with the possibility to leach out from the device to the surrounding tissue present a major problem. Direct wiring of enzymes to electrodes can minimize the oxygen limitation, although this modification adds unwanted complexities and higher expense.

These defects have been rectified by developing a polarographic technique for simultaneous measurement of oxygen and glucose. However, the low sensitivity of the electrode (in the polarographic technique) to oxygen and the involvement of oxygen in the oxidation of other interfering species (i.e., ascorbic acid (AA), acetaminophen (AP), uric acid (UA), and the like) render the method unsuitable for reliable operation. Independent determination of glucose and oxygen concentrations could in principle account for oxygen induced sensor interferences. A number of reports have attempted to account for these, although addition of other sensor element adds additional complexities with respect to sensor integration, testing and calibration.

As mentioned above, an impediment with Clark-type glucose sensors is the fact that a number of endogenous species, such as ascorbic acid (AA), acetaminophen (AP), uric acid (UA), and the like), also oxidize at the same potential as $H_2O_2$ (i.e. 0.6-0.7 V), which can add error to the electrochemical signal. High confidence sensors have to actively account for these species, and at present not many methodologies have been developed. For example, anionic charged membranes based on negatively charged polymers (e.g., NAFION®, polyester sulfonic acid, cellulose acetate, and the like) have shown to exclude interferences from anionic species like ascorbic acid, uric acid, and the like, based on the principle of charge repulsion. However, the large response time associated with these membranes hinders their usage. Another popular approach to eliminate interference signals from endogenous species has been the use of inner, ultra-thin, electropolymerized films between working electrode and enzyme layer. These films have been shown to exert partial screening from interference agents to first generation analyte sensors. However, these electropolymerized films only minimize signal from endogenous species, and eliminating such interference has not been realized. Moreover, these membranes do not possess long term stability, and their interference eliminating property decreases shortly due to swelling of the polymer.

In another approach, secondary enzymes (for example ascorbate oxidase which converts ascorbic acid to dehydroascorbate and water) have been incorporated in the outer membrane of the sensor to eliminate the particular species from reaching the electrode surface and contributing to amperometric current. These secondary enzymes do however use oxygen as a co-substrate and could eventually deplete the sensors from the oxygen that is used for the operation of the primary enzyme (i.e. $GO_x$). In yet another approach, independent determination of these interferences using secondary working electrodes have improved sensor reliability, although, once again, the addition of another sensor adds additional complexities involving sensor integration, testing and failure.

Another major problem associated with these implantable sensors is the changes in the electrocatalytic activity of the working electrodes as well as the in the permeability of the outer membranes after implantation in the body. While the former is a result of product adsorption on the surface of the working electrode, the latter is a result of unwanted accumulation of exogenous reagents within these membranes (i.e., calcification, biofouling, and the like). Such factors lead to decrease in sensitivity, drifts, and to their eventual failure. Moreover, passivation of working electrodes and inhibition of its electro-catalytic activity as result of continuous biasing also leads to saturation in sensor response. To this end, higher applied potentials, double pulsed amperometry or pulsed amperometric detection have been the common strategies to renew the surface of the working electrode even though such techniques are complex to be applied for miniaturized sensors and implantable sensors with miniaturized driving electronics. To date there is no reported methodology to account for such in vivo induced sensor drifts and the ability to internally calibrate the sensor against these variations is paramount for long-term sensor operation.

SUMMARY

Disclosed herein is a device comprising a reference electrode; a counter electrode; a working electrode; the working electrode being disposed in the vicinity of the reference and counter electrode; an electrically conducting membrane; the electrically conducting membrane being in operative communication with the working electrode; an enzyme layer; the enzyme layer being in operative communication with the working electrode; a semi-permeable membrane; the semi-permeable membrane being in operative communication with the working electrode; a first layer of a first hydrogel in operative communication with the working electrode; the first layer of the first hydrogel being operative to store oxygen; wherein the amount of stored oxygen is proportional to the number of freeze-thaw cycles that the hydrogel is subjected to; and a second layer of the second hydrogel in operative communication with the working electrode; the second layer of the second hydrogel comprising tissue response modifying release agents.

Disclosed herein too is a method comprising internally calibrating an electrochemical biosensor based on a primary reaction when the electrochemical biosensor has reached equilibrium; monitoring a departure from equilibrium of a secondary electrochemical reaction; the secondary electrochemical reaction altering a state of a working electrode of the electrochemical biosensor; the secondary electrochemical reaction altering the electrochemistry of the primary reaction.

Disclosed herein too is a method comprising performing periodic biasing amperometry on a sensor, the sensor comprising a reference electrode; a counter electrode; a working electrode; the working electrode being disposed in the vicinity of the reference and counter electrode; an electrically conducting membrane; the electrically conducting membrane being in operative communication with the working electrode; an enzyme layer; the enzyme layer being in operative communication with the working electrode; a semi-permeable membrane; the semi-permeable membrane being in operative communication with the working electrode; the first layer of the first hydrogel in operative communication with the working electrode; the first layer of the first hydrogel being operative to store oxygen; wherein the amount of stored oxygen is proportional to the number of freeze-thaw cycles that the hydrogel is subjected to; and a second layer of a second hydrogel in operative communication with the working electrode; the second layer of the second hydrogel comprising tissue response modifying release agents; the periodic biasing amperometry comprising biasing the working electrode for a short duration of time at regular intervals at a number of testing potentials; repeating the periodic biasing for all the testing potentials; continuing the periodic biasing until a steady state is attained for all the testing potentials; conducting an internal calibration of the sensor after an analyte being measured has reached a steady state; the internal calibration comprising a time interval where the periodic biasing is not applied; measuring a periodic biasing amperometric signal difference immediately before and immediately after the time interval comprises; measuring a differential for the periodic biasing amperometric signal difference; comparing the differential with a calibration chart to obtain sensitivity factors; and applying the sensitivity factors to the sensor to correct against drifts.

Disclosed herein too is a method for supplementing oxygen within a sensor, the supplementing comprising performing multiple freeze-thaw cycles on a first layer of a first hydrogel; the sensor comprising a reference electrode; a counter electrode; a working electrode; the working electrode being disposed in the vicinity of the reference and counter electrode; an electrically conducting membrane; the electrically conducting membrane being in operative communication with the working electrode; an enzyme layer; the enzyme layer being in operative communication with the working electrode; a semi-permeable membrane; the semi-permeable membrane being in operative communication with the working electrode; the first layer of the first hydrogel in operative communication with the working electrode; the first layer of the first hydrogel being operative to store oxygen; wherein the amount of stored oxygen is proportional to the number of freeze-thaw cycles that the hydrogel is subjected to; and a second layer of a second hydrogel in operative communication with the working electrode; the second layer of the second hydrogel comprising tissue response modifying release agents.

DETAILED DESCRIPTION

Figure 1:
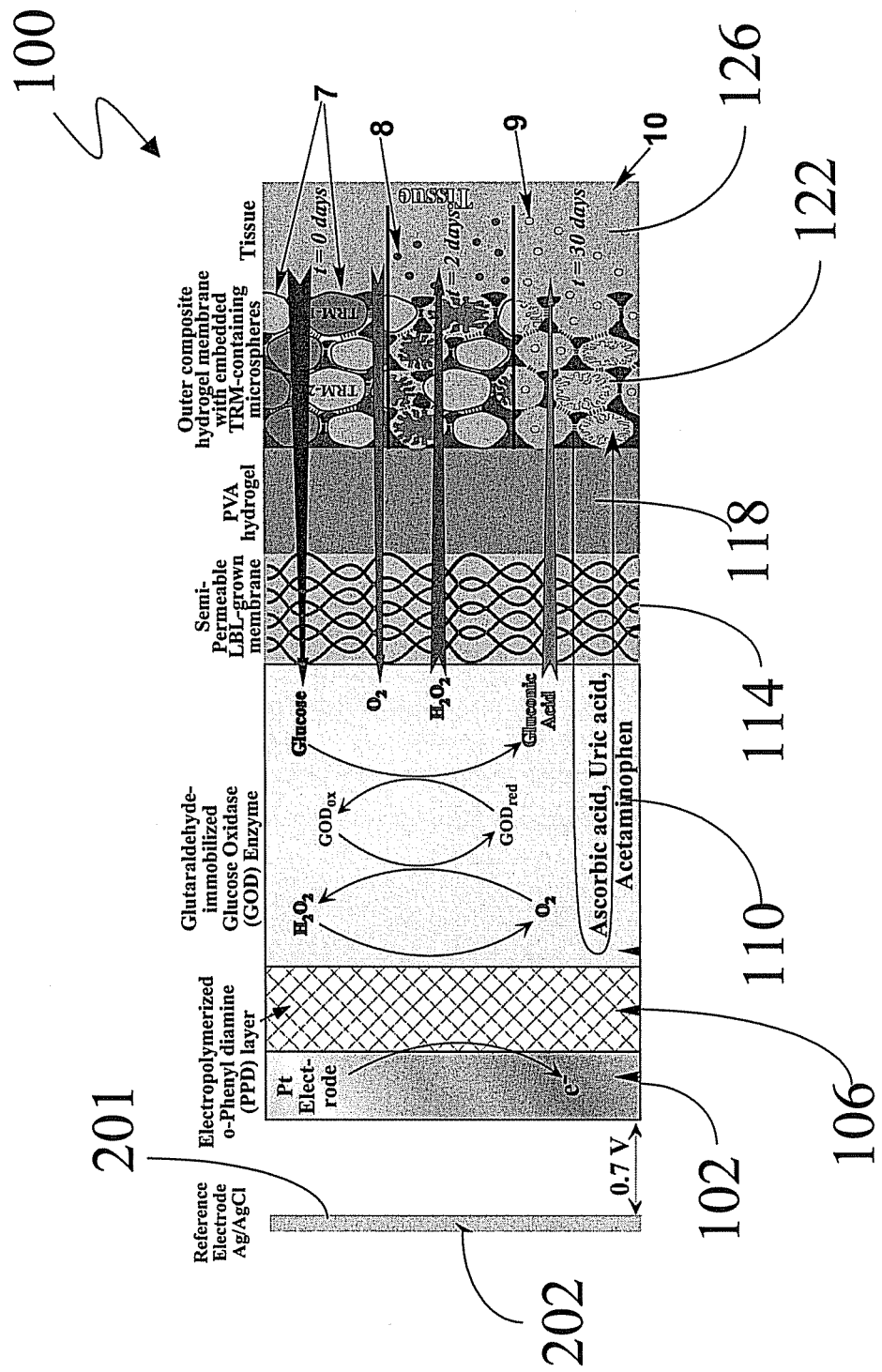
FIG. 1 is a schematic representation of a modified amperometric glucose sensor, along with various chemical, electrochemical and diffusion processes associated with its operation. The glucose oxidase ($GO_x$) layer is coated with a semi-permeable membrane to reduce the amount of glucose entering the sensor. The hydrogel coating shows embedded microspheres at different stages of degradation and release of tissue response modifying (TRM) agents.

Disclosed herein is an implantable glucose sensor (hereinafter sensor or biosensor). The sensor comprises a working electrode in operative communication with an electrically conducting membrane, an enzyme layer, a semi-permeable membrane, a first layer of a first hydrogel and a second layer of the second hydrogel.

In one embodiment, the working electrode comprises a metal upon which is disposed an electrically conducting polymer and an enzyme specific to an analyte of interest (hereinafter the "analyte"), a layer-by-layer film to fine-tune permeability to the analyte, a poly(vinyl alcohol) hydrogel layer to store and provide additional oxygen to the sensor, and a biocompatible coating that are also capable of releasing a variety of drugs. The biosensor is advantageous over other comparative biosensors in that it (a) exhibits high linearity; (b) exhibits high sensitivity; (c) takes into account the contribution of exogenous interfering species; and (d) provides internal calibration routines to take into account sensor drifts based on in vivo induced effects that change the permeability of semi-permeable membrane. It also accounts for gradual decay of electrode activity.

Disclosed too is a method that comprises using periodically biased amperometry towards interrogation of implantable glucose sensors to improve both sensor's sensitivity and linearity while at the same time enable internal calibration against sensor drifts that originate from changes in either electrode activity or membrane permeability as a result of fouling, calcification and/or fibrosis. This method involves the application of a biasing voltage to the working electrode with respect to the neighboring reference electrode for a short duration of time, at controlled intervals. This reduces sensor stressing and enhances long-term stability while at the same time provides better power management and signal to noise ratio. Variations in bias duration and time intervals allow us to modulate the electro-catalytic activity of the working electrode, herein termed as "action". This action is afforded by varying the redox state of the working electrode through the application of specific bias and time duration. The redox state of the working electrode is however reversely affected by the amount of time and concentration of $H_2O_2$ that is adjacent to the electrode, which constitutes a "counter-action" to bias. As it turns out, the concentration of $H_2O_2$ concentration is related to both sub-cutaneous (s.c.) tissue concentration of glucose and the permeability coefficient of semi-permeable membranes adjacent to the electrodes. At constant glucose concentration, the competition of "action" and "counter-action" provides us with the ability to decipher and quantify sensor drifts originating from changes in the permeability of semi-permeable membranes. In a similar manner, the same membrane permeability and different glucose concentration also enables the determination of electrode activity. The combination of these two routines provides the means to internally re-calibrate the implantable sensor against drifts and avoid frequent external calibrations. By varying bias voltage, periodically-biased amperometry together with the aforementioned "action" and "counter-action" from various electroactive analytes (i.e. oxygen, uric acid, acetaminophen, ascorbic acid) can also be utilized to enable their simultaneous detection along with glucose.

FIG. 1 depicts an exemplary configuration of the biosensor 100, which comprises a working electrode 102 in operative communication with an electrically conducting membrane 106, an enzyme layer 110, a semi-permeable membrane 114, a first layer of a first hydrogel 118 and a second layer of the second hydrogel 122. As can be seen in the FIG. 1, the second layer of the second hydrogel composite 122 contacts tissue 126 in a living being. Opposed to the working electrode is a reference electrode 202.

The working electrode 102 generally comprises a metal. In an exemplary embodiment, the metal is an inert metal. Examples of the metal are platinum, gold, palladium, or the like, or a combination comprising at least one of the foregoing metals. Alternatively, the working electrode can comprise carbon. In an exemplary embodiment, the working electrode 102 comprises platinum. The working electrode 102 is opposedly disposed next to reference electrode 202.

The working electrode 102 has an area of about 0.1 square millimeters ($mm^2$) to about 100 $mm^2$. In a preferred embodiment, the working electrode 102 has a thickness of about 0.2 $mm^2$ to about 0.3 $mm^2$. Alternatively, the area of the working can be smaller than 0.1 $mm^2$.

As noted above, the working electrode 102 is in operative communication with an electrically conducting membrane 106. It is desirable for the electrically conducting membrane 106 to prevent the diffusion of a number of endogenous species like ascorbic acid, uric acid and acetaminophen. In one embodiment, the working electrode 102 is in physical communication with the electrically conducting membrane 106. In an exemplary embodiment, the electrically conducting membrane 106 is disposed upon and in intimate contact with the working electrode 102.

The electrically conducting membrane 106 undergoes redox changes depending on the time and duration of the applied voltage as well as the concentration of various soluble redox species that are in its immediate vicinity. In one embodiment, the electrically conducting membrane 106 is an electrically conducting nanocomposite that affords sensitivity to more than one analyte at a various testing potentials.

The electrically conducting membrane can comprise intrinsically electrically conducting polymers and copolymers or polymers that are made electrically conducting by virtue of being filled with a percolating network of electrically conducting particles.

Intrinsically electrically conducting polymers are polypyrrole, polyaniline, polythiophene, polyacetylene, polyphenylene diamine, poly(3,4-ethylenedioxythiophene) poly(styrenesulfonate), sulfonated poly aniline, sulfonated polypyrrole, poly(ethylene dioxythiophene), poly(ethylenedioxypyrrole), poly(p-phenylene vinylene), polycarbazole, substituted polycarbazole, polyindole, or the like, or a combination comprising at least one of the foregoing intrinsically electrically conducting polymers.

The intrinsically conducting polymer can be copolymerized with other insulating organic polymers. Examples of organic polymers that can be copolymerized with the intrinsically conducting polymer are polyacetals, polyacrylics, polycarbonates polystyrenes, polyesters, polyamides, polyamideimides, polyarylates, polyacrylates, polymethylmethacrylates, polyarylsulfones, polyethersulfones, polyphenylene sulfides, polyvinyl chlorides, polysulfones, polyimides, polyetherimides, polytetrafluoroethylenes, polyetherketones, polyether etherketones, polyether ketone ketones, polybenzoxazoles, polyoxadiazoles, polybenzothiazinophenothiazines, polybenzothiazoles, polypyrazinoquinoxalines, polypyromellitimides, polyquinoxalines, polybenzimidazoles, polyoxindoles, polyoxoisoindolines, polydioxoisoindo lines, polytriazines, polypyridazines, polypiperazines, polypyridines, polypiperidines, polytriazoles, polypyrazoles, polypyrrolidines, polycarboranes, polyoxabicyclononanes, polydibenzofurans, polyphthalides, polyacetals, polyanhydrides, polyvinyl ethers, polyvinyl thioethers, polyvinyl alcohols, polyvinyl ketones, polyvinyl halides, polyvinyl nitriles, polyvinyl esters, polysulfonates, polysulfides, polythioesters, polysulfones, polysulfonamides, polyureas, polyphosphazenes, polysilazanes, polysiloxane, polyolefins, or the like, or a combination comprising at least one of the foregoing organic polymers.

As noted above, the electrically conducting membrane 106 can comprise an electrically insulating organic polymer that is filled with electrically conducting filler. Examples of electrically conducting fillers are carbon nanotubes, carbon black, carbon nanoparticles, nanorods, intrinsically electrically conducting polymer powders, metal powders, electrically conducting ceramic powders, or the like, or a combination comprising at least one of the foregoing electrically conducting fillers. Other fillers that can be used in the electrically conducting membrane 106 are nano-sized inorganic compounds, nano-sized inorganic (e.g., $TiO_2$), Au, Ag, Rd, Pd, or Pt nanoparticles, $SnO_2$ nanoparticles, $SnO_2$ nanorods, $SiO_x$ nanoparticles, or the like, or a combination comprising at least one of the foregoing nanoparticles.

In one embodiment, the electrically conducting membrane 106 can comprise conducting polymers that are copolymers of (3,4-dihydroxy-L-phenylalanine), hydroxyquinones, ferrocene and ferrocene derivatives, ferricyanide, tetrathiafulvalene-tetracyanoquinodimethane, osmium salts, phenothiazine, phenoxazine, porporphorins, flavins, pyroloquinoline quinines, or the like, or a combination comprising at least one of the foregoing copolymers.

In another embodiment, the electrically conducting membrane 106 can comprise redox enzymes; the redox enzymes being horseradish peroxidase, myoglobin, glucose dehydrogenase, or the like, or a combination comprising at least one of the foregoing redox compounds.

In one embodiment, the electrically conducting membrane 106 can comprise redox enzymes in an amount of about 1 to about 99 weight percent (wt %), specifically about 2 to about 95 wt %, and more specifically about 5 to about 80 wt %, based on the total weight of the electrically conducting membrane.

The electrically conducting membrane 106 can be spin coated, crosslinked, inkjet printed and patterned on top of the working electrode 102. In one embodiment, the inkjet printed nanocomposite is crosslinked. The crosslinking can be attained by inkjet printing crosslinking agents or the crosslinking can be conducted by immersing the device into crosslinking agents.

In an exemplary embodiment, the electrically conducting membrane 106 can be constructed by electropolymerizing a thin layer of ortho-phenylene diamine (OPD) to yield poly (ortho-phenylene diamine) (PPD). In another exemplary embodiment, the electrically conducting membrane 106 can be manufactured by electropolymerizing a thin layer of PPD in the presence of electrically conducting nanotubes and/or nanorods. The nanotubes, nanowires and/or the nanorods are embedded in the thin layer of PPD. Examples of nanotubes are multiwall carbon nanotubes (MWNTs), single wall carbon nanotubes (SWNTs), or a combination comprising at least one of the foregoing carbon nanotubes. Examples of nanorods are aluminum nanorods, copper nanorods, or the like, or a combination comprising at least one of the foregoing nanorods.

In one embodiment, the electrically conducting membrane 106 can comprise nanoparticles or nanotubes in an amount of about 1 to about 99 weight percent (wt %), specifically about 2 to about 95 wt %, and more specifically about 5 to about 80 wt %, based on the total weight of the electrically conducting membrane.

In yet another exemplary embodiment, the electrically conducting membrane 106 can be realized by first assembling a plurality of shortened single-walled carbon nanotubes and subsequently electropolymerizing around it a thin layer of PPD.

The electrically conducting membrane 106 has a thickness of about 5 to about 100 nanometers. In a preferred embodiment, the electrically conducting membrane 106 has a thickness of about 10 to about 20 nanometers.

The electrically conducting membrane 106 is in operative communication with an enzyme layer 110. In one embodiment, the enzyme layer 110 comprises glucose oxidase, lactate oxidase, poly vinyl alcohol (PVA), bovine serum albumin, or the like, or a combination comprising at least one of the foregoing materials. In another embodiment, the enzyme layer 110 is crosslinked with glutaraldehyde. The enzyme layer 110 may comprise a conductive polymer if desired. In an exemplary embodiment, the enzyme layer 110 is a glucose oxidase ($GO_x$) enzyme layer 110.

In one embodiment, the electrically conducting membrane 106 is in physical communication with a glucoseoxidase ($GO_x$) enzyme layer 110. In another embodiment, the glucoseoxidase ($GO_x$) enzyme layer 110 contacts a surface of the electrically conducting membrane 106 that is opposed to the surface in contact with the working electrode 102. The glucoseoxidase ($GO_x$) enzyme layer 110 is immobilized on the electrically conducting membrane and is hence referred to as the immobilized glucoseoxidase ($GO_x$) enzyme layer 110.

Within the immobilized glucoseoxidase ($GO_x$) enzyme layer 110, glucose reacts with oxygen ($O_2$) to produce hydrogen peroxide in accordance with reaction (1) detailed above. The generated hydrogen peroxide is anodically (with respect to the reference electrode 202) detected at the working electrode 102.

In one embodiment, the enzyme layer 110 is electropolymerized on top of the electrically conducting membrane 106. In another embodiment, the electrically conducting membrane 106 and the enzyme layer 110 are electropolymerized concurrently.

The immobilized glucoseoxidase ($GO_x$) enzyme layer 110 has a thickness of about 1 nanometer to about 1,000 micrometers. In a preferred embodiment, the immobilized glucoseoxidase ($GO_x$) enzyme layer 110 has a thickness of about 10 nanometers to about 100 micrometers.

In order to regulate the amount of glucose with respect to oxygen and ensure better sensor linearity, the immobilized glucoseoxidase ($GO_x$) enzyme layer 110 is in operative communication with a semi-permeable membrane 114. In one embodiment, the immobilized glucoseoxidase ($GO_x$) enzyme layer 110 is in physical communication with a semi-permeable membrane 114. In another embodiment, the immobilized glucoseoxidase ($GO_x$) enzyme layer 110 is disposed upon and in intimate contact with a semi-permeable membrane 114. The immobilized glucoseoxidase ($GO_x$) enzyme layer 110 is disposed upon a surface of the semi-permeable membrane that is opposed to the surface that contacts the electrically conducting membrane 106.

The semi-permeable membrane 114 comprises alternating layers of positive and negative polyion species (i.e., polymers, oligomers and/or multi-valent cations) stacked in a layer-by-layer (LBL) fashion. Variations in the number of LBL-deposited bi-layers have been shown to regulate the inward diffusion of glucose and outward diffusion of hydrogen peroxide.

The semipermeable membrane 114 can comprise a plurality of alternating layers of a poly acid and metal ions. The alternating layers are also termed multilayers. The poly acid can be a polymeric acid or a non-polymeric inorganic acid. In one embodiment, the poly acid is humic acid while the metal ions are $Fe^{3+}$.

The semipermeable membrane can also comprise polystyrene sulfonate, polydimethyl diallyl ammonium chloride, polyethyleneamine, hyaluronic acid, polyaspartic acid, polylysine, chitosan, collagen, or the like, or a combination comprising at least one of the foregoing materials. The semipermeable membrane is manufactured through layer-by-layer assembly. In one embodiment, the semipermeable membrane is patterned on top of the working electrode. In another embodiment, the semipermeable membrane is ink jet printed in layer-by-layer fashion with intermediate washing steps.

The semipermeable membrane comprises 1 multilayer to 1,000 multilayers, specifically about 3 to about 100 multilayers, and more specifically about 5 to about 10 multilayers.

The semi-permeable membrane 114 has a thickness of about 2 to about 1000 nanometers. In a preferred embodiment, the semi-permeable membrane 114 has a thickness of about 2 to about 100 nanometers.

In order to immobilize and locally deliver various tissue response modifying (TRM) agents that control and suppress inflammation of the surrounding tissue, while at the same time permitting passage of glucose and $O_2$, a hydrogel coating can be incorporated on the surface of the sensor that contacts the surface of the tissue 106. In one embodiment, the hydrogel coating comprises a first layer of a first hydrogel 118 and a second layer of the second hydrogel 122.

As can be seen in the FIG. 1, the first layer of hydrogel 118 is in operative communication with the semi-permeable membrane 114, while the second layer of hydrogel 122 is in operative communication with the first layer of hydrogel 118. In another embodiment, the first layer of hydrogel 118 is in physical communication with the semi-permeable membrane 114, while the second layer of hydrogel 122 is in physical communication with the first layer of hydrogel 118.

In an exemplary embodiment, the first layer of hydrogel 118 is disposed upon and in intimate contact with a surface of the semi-permeable membrane 114 that is opposed to the surface in contact with the immobilized glucose oxidase ($GO_x$) enzyme layer 110. The first layer of hydrogel 118 generally comprises a water-soluble polymer that can absorb oxygen. It is desirable for the first layer of hydrogel 118 to be crosslinked. In one embodiment, the first layer of hydrogel 118 is crosslinked by freeze-thaw pumping. The number of freeze-thaw pumping cycles can be varied.

In one embodiment, the number of freeze-thaw pumping cycles can be varied from about 1 to about 25 cycles. In an exemplary embodiment, the number of freeze-thaw pumping cycles can be varied from about 1 to about 7 cycles.

The first hydrogel can be the same or different as the second hydrogel. Examples of the first and second hydrogels are crosslinked polyhydroxyethylmethacrylate, polyethylene oxide, polyacrylic acid, polyvinylpyrrole, chitosan, collagen, or the like, or a combination comprising at least one of the foregoing hydrogels.

In one embodiment, the first layer of the first hydrogel 118 and the second layer of the second hydrogel 122 both comprise polyvinylalcohol (PVA). The PVA ensures a homogeneous coverage of the immobilized glucoseoxidase ($GO_x$) enzyme layer 110. It also facilitates the storage of $O_2$. In an exemplary embodiment, the amount of stored $O_2$ is controlled by varying the number of freeze-thaw cycles for the PVA. In another exemplary embodiment, this PVA layer can be loaded with various oxygen storing enzymes (e.g., myoglobin) and oxygen producing enzymes (e.g., catalase).

The hydrogel membrane is spun coated, crosslinked and patterned on top of the working electrode. In one embodiment, the hydrogel membrane is inkjet printed on top of the working electrode.

The second layer of the second hydrogel 122 is in operative communication with the first layer of the first hydrogel 118. In one embodiment, the second layer of the second hydrogel 122 is in physical communication with the first layer of the first hydrogel 118. In an exemplary embodiment, the second layer of the second hydrogel is disposed upon and in intimate contact with a surface of the first layer of the first hydrogel 118 that is opposed to the surface in contact with the semipermeable membrane 114.

The second layer of the second hydrogel 122 contains tissue response modifying (TRM) release agents. The TRM can be a composite of PVA and TRM containing PLGA microspheres. The second layer of hydrogel can also be crosslinked by freeze-thaw pumping. In one embodiment, the second layer of hydrogel 122 is a composite that comprises a water-soluble polymer in addition to TRM microspheres. In another embodiment, the water-soluble polymer of the second layer of hydrogel 122 is also polyvinylalcohol. A surface of the second layer of hydrogel 122 generally contacts the tissue 126 of a living being. The gradual release of TRM is assisted by the degradation of microspheres (7) that contain various drugs. As can be seen in the FIG. 1, the TRM releases these drugs over a period of time (see 7, 8 and 9 in the FIG. 1). The concentration of the TRM in the second layer of hydrogel 118 can be varied.

In general, the first layer of hydrogel 118 and/or the second layer of hydrogel 122 can comprise a variety of enzymes to eliminate endogenous species. Examples of the enzymes are catalase, transferase, hydrolase, oxidase, peroxidase, kinases, superoxidase, phosphatase, transferase, hydrolase, pyrophosphatase, oxygenase, nuclease, lipase, peptidase, trancacetylase, hydroxylase, dioxygenase, dehydrogenase, carboxylase, aminase, catalase, phosphohydrolase, diaminase, reductase, synthase, kinase, caspase, methionine synthase, cystathionase, or the like, or a combination comprising at least one of the foregoing enzymes.

In one embodiment, the PVA layer can contain a variety of different additives. Examples of such additives are myoglobin, nanotubes, nanorods, or the like, or a combination comprising at least one of the foregoing additives. In one embodiment, the combination of catalase and myoglobin is varied in an amount of about 1 to about 99 weight percent (wt %), based on the total weight of the first layer of hydrogel 118 and/or the second layer of hydrogel 122.

In general in comparative devices, the sensor is subjected to an amperometric testing methodology that relies on a continuous biasing of the working electrode. This testing is conducted to determine the calibration of the sensor, which in turn dictates the working of the sensor and the infusion of insulin or glucose into the body of a living being. In general, in order to effect calibration and functioning of the sensor in this manner, the electrical current response with time is used to determine the amount of insulin or glucose that should be injected into the living being.

It is believed that this testing methodology ensures that all transient effects have been eliminated and proper diffusion gradients have been established between the reactants and products of the electrochemical half reaction that are brought about by the biosensor. However, continuous biased amperometry subjects the sensor to sensor-stress that eventually leads to signal decay. This signal decay occurs because of drift in readings at the working electrode. However, additional drifts can originate from changes in permeability of the semi-permeable membranes that are located between the working electrode and the tissue as well as because of changes in the electro-activity of the working electrode.

In general, continuous biased amperometry leads to a much smaller signal that is the result of the reduced availability of the analyte(s), over saturation of the half reaction byproduct(s) and/or suppressed electroactivity of the electrode due to the higher presence of these byproduct(s) is produced. As a result, this smaller signal is generally compensated for by using a (i) higher applied potential (ii) double pulsed amperometry and/or (iii) pulsed amperometric detection. Each of these methods of compensation, however, uses higher voltages (which exacerbate signals from exogenous species). In addition, double pulse amperometry utilizes complex driving electronics, difficult to attain for miniaturized implantable devices.

Figure 2:
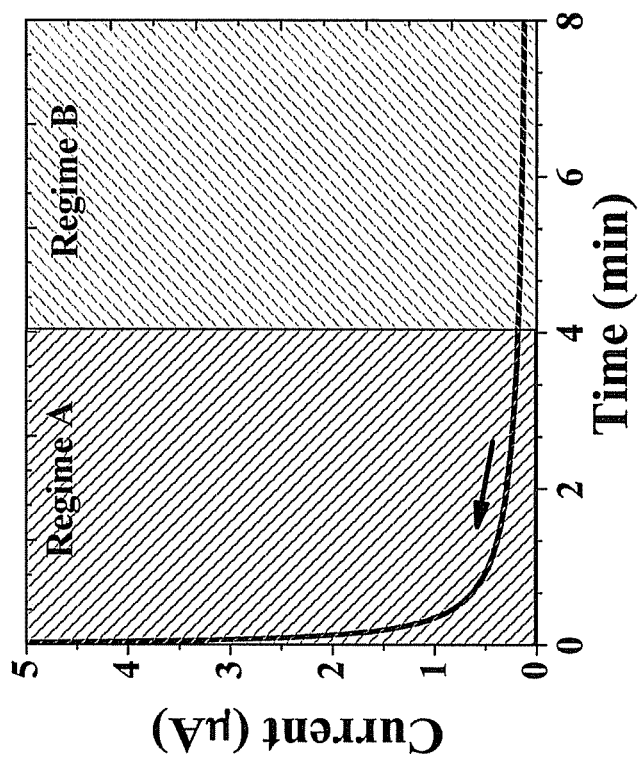
FIG. 2 is a graphical amperometric response for an electrochemical sensor as function of voltage-biasing duration. This response exhibits two operational regimes; (A) non-equilibrated regime and (B) equilibrated regime. Upon cessation of voltage biasing along with exposure to redox-active agents (i.e., $H_2O_2$, $O_2$, $H_2O$, and the like) the amperometric response of the sensor will start shifting upwards along the indicated arrow. The departure from the equilibrium will depend on the cessation duration of the voltage-bias and concentration of redox-active agent(s)

An exemplary response of an unused new sensor (or a sensor that has not been operated for a long period of time) that is subjected to this type of amperometric testing involving voltage biasing as function of time is illustrated in FIG. 2. This response exhibits two operational regimes: (A) non-equilibrated regime that shows a rapid "run in" signal decay followed by a gradual equilibration to enter regime B, where its response is equilibrated. The signal displayed in the FIG. 2 can be a response to exposure to any redox-active agents such as $H_2O_2$, $O_2$, $H^+$, and the like. Upon termination of voltage biasing, along with exposure to redox-active agents (i.e. $H_2O_2$, $O_2$, $H_2O$, and the like), the amperometric response of the sensor gradually starts moving backwards to the non-equilibrated regime A. This departure from the equilibrium depends on the time duration for which the voltage biasing has been switched off. The departure from the equilibrium also depends on the concentration of redox-active species in the vicinity of the electrode. Since these redox-active species are in constant equilibrium with the subcutaneous tissue (e.g., 126 in the FIG. 1) (via diffusion through a number of semi-permeable membranes, which also includes those generated by an immuno-response) it provides a means of accessing and assessing the diffusion characteristics of the membrane while the sensor is in an in vivo operation.

Figure 3:
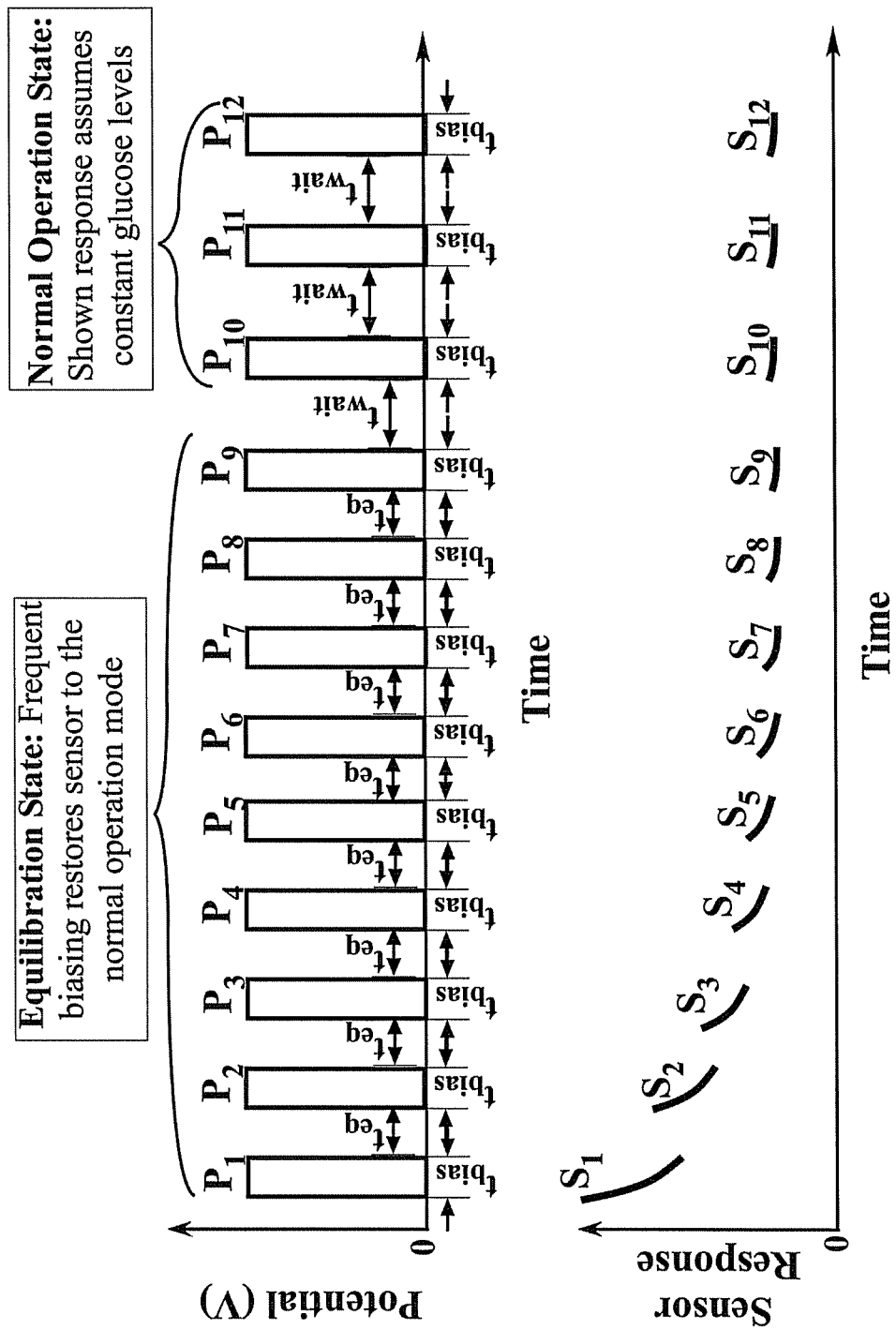
FIG. 3 is a graphical response depicting the applied bias/measuring time sequence employed in the periodically-biased amperometric testing of glucose sensors.

In order to avoid the signal run-up and the subsequent decay during calibration of the sensor, it is desirable for the sensor to be operated in a periodic biasing mode with time periods long enough to allow for equilibration. FIG. 3, illustrates one exemplary periodic biasing operation which permits equilibration of the sensor so that a new normal sensor operation state is developed. This operation state is used to avoid the aforementioned run-ups and decays that are depicted in the FIG. 2.

For purposes of simplicity, responses are depicted for glucose concentration kept the same throughout the time period of experimentation shown in FIG. 3. Throughout the amperometric testing that includes sensor biasing, the biasing steps are performed for a short duration of time (e.g., a period of about 1 second) and preferably kept the same throughout the sensor operation, unless otherwise stated. Initially, the sensor response has to be "partially" equilibrated, as depicted in regime A of FIG. 2. This is performed with periodic biasing (as depicted by $t_{eq}$) shown in FIG. 3. The resulting signals from the periodic biasing steps correspond to sections of the current-time curve shown in FIG. 2, regime A. From the FIG. 3 (steps $P_1$ through $P_8$), it can be seen that the signal at the end of a given biasing period is slightly lower than the initial signal value of the next biasing period. This effect arises from the aforementioned exposure of the sensor to the redox-active species that are constantly replenished at the vicinity of the electrode and therefore attempt to relax the sensor to its initial state. Eventually, after a number of equilibration biasing steps (herein shown in nine steps, $P_1$ to $P_9$) the sensor response reaches a steady state. At this point normal sensor operation (or equilibration) ($P_{10}$ to $P_{12}$), is established and after the establishing of this equilibration, the interval between biasing steps can be varied or controlled to reduce sensor stress and consequent error.

In an exemplary embodiment, the interval (e.g., $t_{wait}$ as seen between $P_{10}$ to $P_{12}$ in the FIG. 3) between biasing steps (can be increased from the intervals established initially (e.g., $t_{eq}$ as seen between $P_1$ to $P_9$) to reduce sensor stress. In another exemplary embodiment, the interval between biasing steps can be decreased from the intervals established initially to reduce sensor stress. When sensor stress and the sequence of signal run-ups and decays are reduced as much as possible, it is then desirable for a computer processing unit (that it in communication with the sensor) to direct the sensor to begin calibration operations. This will be discussed below.

Figure 4:
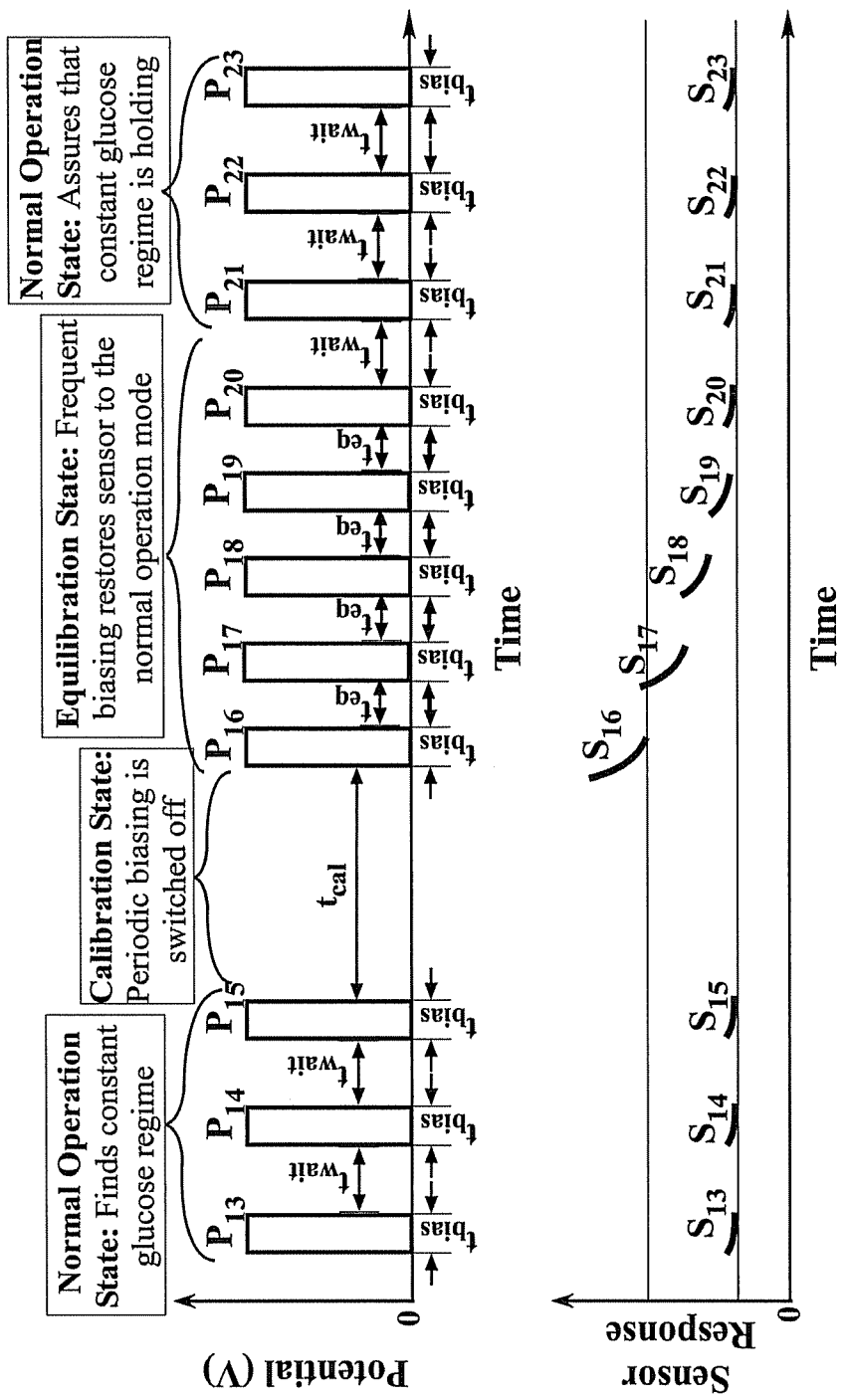
FIG. 4 is a graphical calibration sequence for assessing changes in the permeability of semi-permeable membranes for prolonged in vivo sensor use. The top panel illustrates the periodic bias sequence for performing this calibration. The bottom panel depicts the expected amperometric response, with the permeability constants inversely proportional to the difference between responses $S_{15}$ and $S_{16}$ for a given $t_{cal}$ interval.

FIG. 4 illustrates one embodiment of a sensor biasing sequence in order to perform an internal calibration routine to assess changes in permeability of the membrane(s) that are disposed upon the sensor as seen in the FIG. 1. It is first desirable to assess a time regime where glucose concentration levels are fairly constant. In general, this time regime occurs during periods of extensive rest where the patient has not consumed a meal prior to the testing. Such a constant glucose concentration regime can be established by assessing the similarity of responses shown for biasing steps $P_{13}$ to $P_{15}$ and as described in the aforementioned paragraphs. Assuming that the end points of $S_{13}$, $S_{14}$, and $S_{15}$ are fairly constant, then a computer processing unit can instruct the sensor to proceed to the calibration state.

For this, the sensor is left unbiased for an extended period of time (e.g., $t_{cal}=n \cdot t_{wait}$, where n varies from about 2 to about 10, where $t_{wait}$ is the waiting time period between measurements and $t_{cal}$ is the calibration time where the periodic biasing is switched off). During this time, redox-active species act on the sensor and increase changes its electrical current response upwards along the lines of the current-time curve shown in regime A of the FIG. 2. At the end of $t_{cal}$, the biasing step $P_{16}$ interrogates in the relaxed sensor and records the $S_{16}$ sensor response. By comparing the end points of $S_{15}$ and $S_{16}$, the magnitude of the departure from equilibrium is established (shown by two horizontal lines in FIG. 4).

In the case depicted in the FIG. 4, the end-point at the equilibrium state for $S_{16}$ is greater than the end-point at the equilibrium state for $S_{15}$. The difference between the end-points is considered to be a positive difference and can be used to facilitate a calibration of the sensor. In a similar manner it is possible for the end-point at the equilibrium state for $S_{16}$ to be lower than the end-point at the equilibrium state for $S_{15}$. This difference will be negative and can also be used to facilitate calibration of the sensor.

At this point, the sensor is brought back to equilibrium to assess if the glucose concentration remained the same during the calibration step. Rapid equilibration takes place in an equivalent fashion to sensor equilibration following implantation, as shown in FIG. 3 ($S_1$ to $S_9$). For example, this rapid equilibration is shown within five biasing steps ($P_{16}$ to $P_{20}$) in FIG. 4. Subsequently, normal sensor operation is established as shown by biasing steps $P_{21}$ to $P_{23}$. Assuming that the sensor response indicated by the end points of $S_{21}$ to $S_{23}$ curves is comparable to end points of $S_{13}$ to $S_{15}$ curves, then the calibration routine is accepted. If the latter in not true, then the calibration routine is not accepted and the driving computer processing unit is instructed to seek another constant glucose regime to re-perform this calibration.

Upon acceptance of the calibration routine, the driving computer processing unit stores the recorded difference between the end point of $S_{15}$ and $S_{16}$ curves ($A_n$, where $n=t_{cal}/t_{wait}$) and compares it to a calibration chart that is already stored in its memory. This chart has been established by a careful in vitro calibration study described below.

Starting with a sensor having a $Pt/PPD/GO_x/(LBL)_m$ configuration, as represented by the layers 102, 106, 110 and 114 of the FIG. 1, the $A_{n,m}$ values (where $n=t_{cal}/t_{wait}$ and m corresponds to the number of LBL bilayers) will be determined as a function of constant glucose concentration (i.e., $S_{15}=S_{23}$) over the entire physiological glucose range (of about 2 to about 22 millimolar (mM)).

Subsequently, the number of LBL bilayers can be varied and a similar study conducted to determine the $A_{n,m+1}$ values to emulate in vivo induced pore clogging of semipermeable membranes. An independent determination of the permeability coefficients ($D_m$) of these $(LBL)_m$ membranes, will permit a correlation of $A_{n,m}$ values with $D_m$ for glucose and $H_2O_2$ and derive an empirical relationship between $A_{n,m}$ and related sensitivity factors. This empirical function will be fed into the operating program of the driving computer processing unit. Following an internal calibration routine, the computer will assess the obtained $A_n$ value with that of the previously stored one. In the case of this calibration being performed for the first time, the $A_n$ value will be compared to that obtained from a calibration routine performed immediately before implantation. That $A_n$ value will be correlated with the $A_{n,m}$ values (obtained from the in vitro testing) to provide a direct relationship to permeability of the semipermeable membranes. Subsequently, and with the help of the stored $A_{n,m}$ values, the sensor sensitivity factors will be updated immediately after every successful internal calibration routine.

Figure 5:
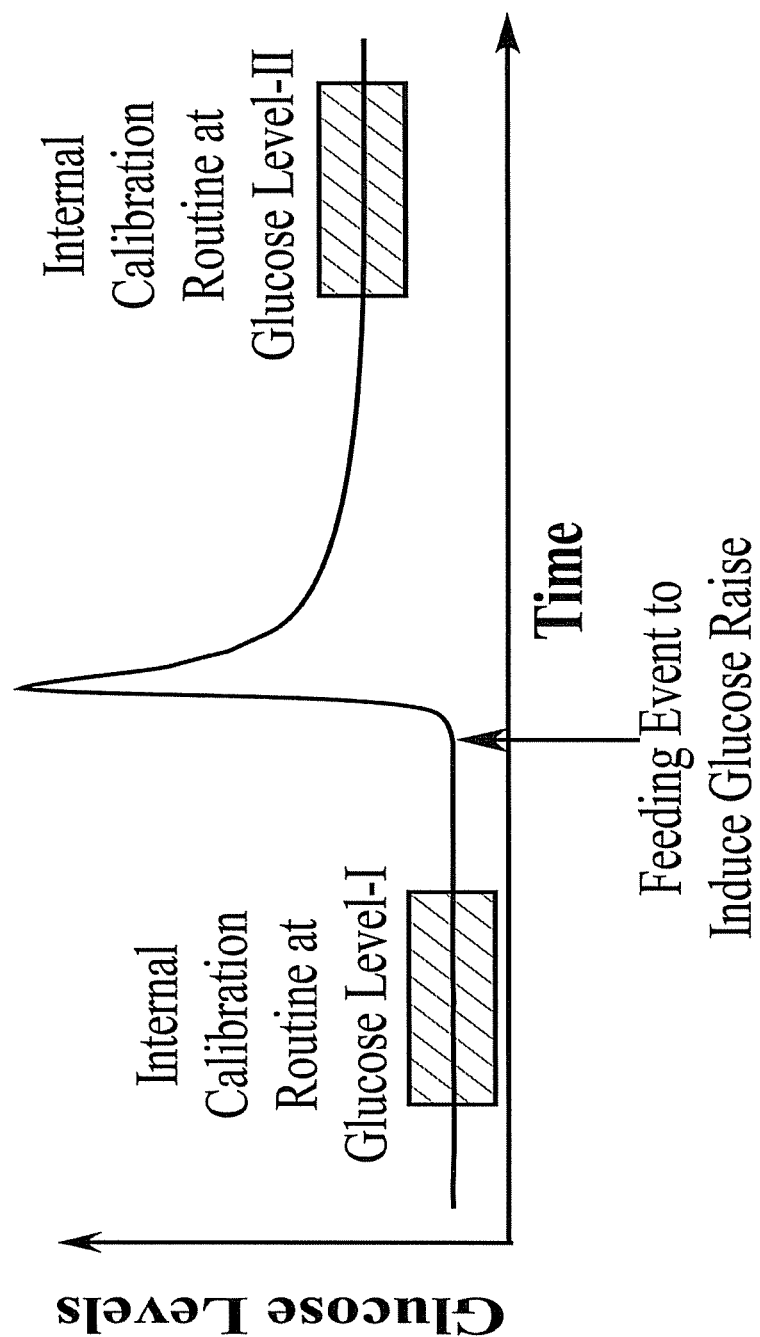
FIG. 5 is a graphical calibration routine for assessing changes in the electrocatalytic activity of the sensor electrodes. Following an internal calibration sequence similar to that of the FIG. 4, a feeding event is conducted. Upon glucose-level equilibration following the feeding event, a calibration sequence similar to FIG. 4 is commenced. Knowing that the permeability of semi-permeable membranes does not change substantially, the change in the assay reading is proportional to the electrocatalytic activity of the sensor electrodes.

FIG. 5 illustrates one embodiment of performing an internal calibration routine to assess changes in the electrode's activity as a function of operation. First, as noted above, it is desirable to assess a time regime where glucose concentration levels are fairly constant. When this is achieved, a first internal calibration routine is conducted upon a user having a first constant glucose level (level-I) to acquire a value for $A_{nI}$. Upon acceptance of this routine at the first constant glucose level the user is instructed to eat a particular meal that raises his/her glucose levels to a second constant glucose level (level-II). A second calibration routine is then performed at the second constant glucose level to acquire a value for $A_{nII}$. Following acceptance of the second calibration routine, the computer compares the $A_{nI}$ with the $A_{nII}$ values. Since the two calibration routines have been performed within a short duration, it is safe to assume that the permeability of the sensor's semipermeable membranes remains constant. Based on this, the difference between $A_{nI}$ and $A_{nII}$ provides an indication of changes in electrode activity. Such changes in electrode activity will be assessed by in vitro calibration where the sensors have been interrogated for extended periods of time. This calibration chart will be stored into the operating program of the driving computer processing unit and utilized to re-adjust the sensor sensitivity immediately after completion of this calibration sequence.

In another embodiment, performing an internal calibration routine to assess changes in the electrode's activity as a function of operating time can originate by tracking the shape and slope of the sensor response during each measurement, and in particular immediately after the calibration state. This time-resolved shape and slope of the response curve is intimately dependent upon the electrode activity. In order to accomplish this it is desirable to have fast electronics and storage capability to (i) record, (ii) store, and (iii) compare the time-resolved decay at each glucose concentration. With the help of an advanced computer, this function can be readily accomplished and compared with a calibration chart (obtained as described above) to extract the electrode activity and recalibrate the sensor. In yet another embodiment, a calibration routine can be performed by using a single $t_{bias}$ measurement; $t_{bias}$ being the time that the sensor is subjected to the biasing voltage. This single measurement is recorded, stored and compared against the $P_{16}$ results at the final and mid point of the curve.

In yet another embodiment, an internal calibration routine to assess changes in the electrode's activity as a function of operation can originate by comparing two sequential calibration steps shown in FIG. 5 performed on the same glucose concentration. The difference between the two calibration steps arise by varying the $t_{bias}$ of the two $P_{16}$ steps. For example, the second $P_{16}$ step can be half or quarter of the first $P_{16}$ step. By recording the corresponding end points of the two $S_{16}$ curves, their difference corresponds to the slope of the $S_{16}$ curve. This slope is dependent on the activity of the electrode and can be readily assessed by an in vitro calibration study routine obtained by sensors that have been subjected for extended periods of time and interrogated with two $t_{bias}$ times at various glucose concentrations. This calibration chart will also be stored in the operating program of the driving computer processing unit and will be used to compare and re-adjust sensor sensitivity with respect to electrode activity.

The periodic biased chronoamperometry is performed by biasing the working electrode for about 1 microsecond to about 10 seconds, specifically about 10 microseconds to about 5 seconds and more specifically about 100 microseconds to about 1 second. In one embodiment, the biasing of the working electrode is conducted at regular periods of greater than or equal to about 5 minutes.

Figure 6:
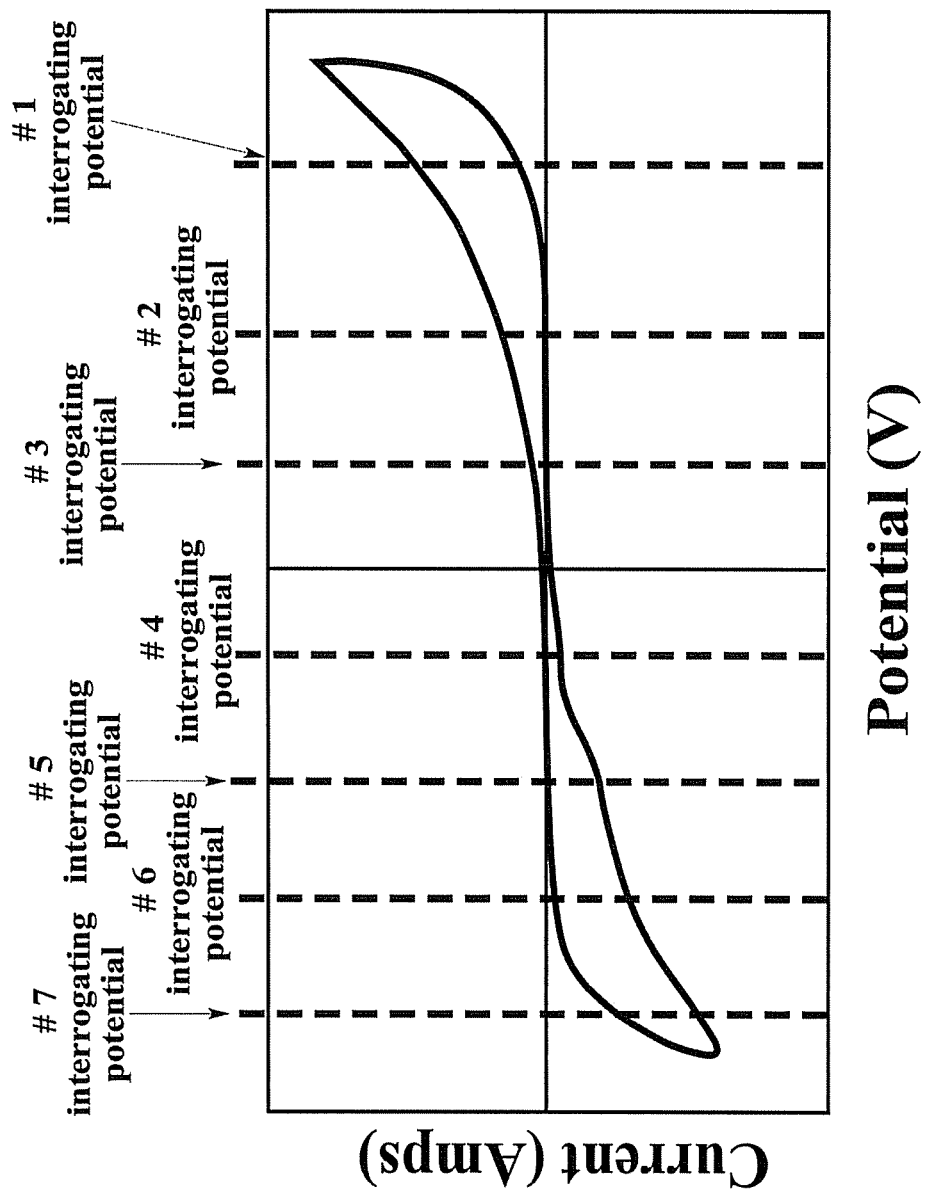
FIG. 6 is a cyclic voltammogram of an electrochemical sensor containing a composite of sensing elements. The sequential interrogation of this sensor at various biasing potentials (shown by broken lines), where different analytes contribute to the amperometric signal to different extents, provide the means to accessing the individual concentrations of various analytes.

To further enhance the reliability of the sensor and to also account for interferences from exogenous species, the sensor can be interrogated at various potentials. FIG. 6 illustrates a typical cyclic voltammogram of an electrochemical sensor containing a composite of sensing elements (i.e. ascorbic acid at #3, acetaminophen, uric and ascorbic acid at #2, glucose and all of previous three at #1, $O_2$ at #4, $O_2$ and $H_2O_2$ at #5, and so on).

Based on this sequential interrogation of the sensor at various biasing potentials (depicted by the broken lines in FIG. 6), it can be seen that since different analytes contribute to the amperometric signal to different extents, this provides a means to accessing the individual concentrations of various analytes. It is to be noted that in order to perform amperometry at different potentials, sensor equilibration is desirable at each potential, as shown for the one potential in FIG. 2.

Figure 7:
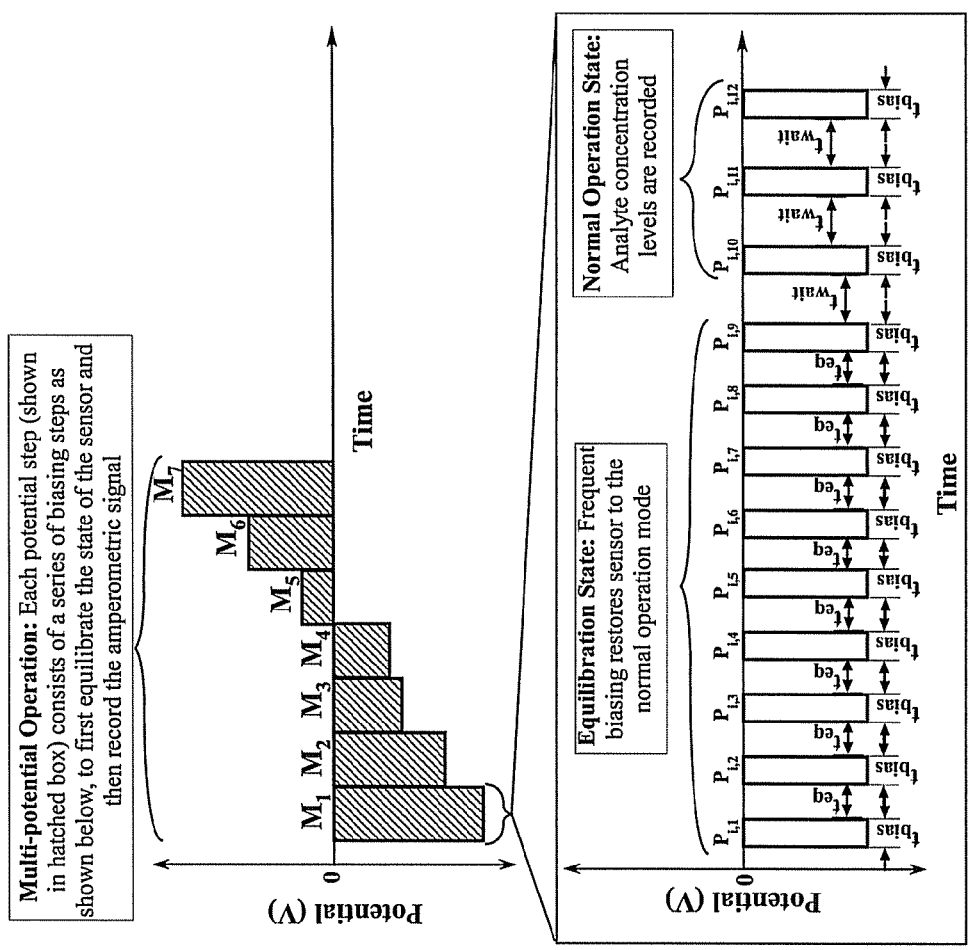
FIG. 7 is a graphical schematic of the applied bias/measuring time sequence employed in multi-analyte detection, using periodically-biased amperometric testing at various potentials.

The multi-component complexity of such measurements can be substantially simplified if the glucose concentration remains fairly constant. Using this information and following similar procedures to that described above in reference to the periodic biasing for sensor equilibration and measurement of FIG. 3, one has to repeat this for each interrogating potential. This is schematically shown in FIG. 7. A matrix formulation routine can be utilized to deduce and solve $n^{th}$ order parametric equations involving the dependence of the response of the glucose sensor on these interfering species. The response of the sensor at a particular interrogating potential (following sensor equilibration) is dependant on $t_{bias}$, $t_{wait}$, and the permeability of the sensor's semi permeable membrane. This being the case, the response of the sensor at a particular interrogating potential can be written as follows:

$$\sum_{i=1}^{i=n} C_{1i} x^i + \sum_{j=1}^{j=n} C_{1j} y^j + \sum_{k=1}^{k=n} C_{1k} z^k + \ldots +$$

$$\sum_{i=1}^{i=n} \sum_{j=1}^{j=n} C_{1ij} x^i y^j + \sum_{i=1}^{i=n} \sum_{k=1}^{k=n} C_{1ik} x^i z^k + \sum_{j=1}^{j=n} \sum_{k=1}^{k=n} C_{1jk} y^j z^k +$$

$$\sum_{i=1}^{i=n} \sum_{j=1}^{j=n} \sum_{k=1}^{k=n} C_{1ijk} x^i y^j z^k + \ldots + C_1 = 0$$

$$\sum_{i=1}^{i=n} C_{2i} x^i + \sum_{j=1}^{j=n} C_{2j} y^j + \sum_{k=1}^{k=n} C_{2k} z^k + \ldots + \sum_{i=1}^{i=n} \sum_{j=1}^{j=n} C_{2ij} x^i y^j +$$

$$\sum_{i=1}^{i=n} \sum_{k=1}^{k=n} C_{2ik} x^i z^k +$$

$$\sum_{j=1}^{j=n} \sum_{k=1}^{k=n} C_{2jk} y^j z^k \sum_{i=1}^{i=n} \sum_{j=1}^{j=n} \sum_{k=1}^{k=n} C_{2ijk} x^i y^j z^k + \ldots + C_2 = 0$$

$$\vdots$$

$$\sum_{i=1}^{i=n} C_{mi} x^i + \sum_{j=1}^{j=n} C_{mj} y^j + \sum_{k=1}^{k=n} C_{mk} z^k + \ldots +$$

$$\sum_{i=1}^{i=n} \sum_{j=1}^{j=n} C_{mij} x^i y^j + \sum_{i=1}^{i=n} \sum_{k=1}^{k=n} C_{mik} x^i z^k + \sum_{j=1}^{j=n} \sum_{k=1}^{k=n} C_{mjk} y^j z^k +$$

$$\sum_{i=1}^{i=n} \sum_{j=1}^{j=n} \sum_{k=1}^{k=n} C_{mijk} x^i y^j z^k + \ldots + C_m = 0$$

where m is the number of interrogating potentials, x, y, z ... are the respective analyte concentrations, i, j, k are the power law dependence (or any other mathematical functions) of the analyte concentrations, and $C_m$ are constants for a particular analyte or analyte overlapping sets and is given as follows:

$$C_m = f\begin{pmatrix} t_{bias}, t_{wait}, \text{permeability of various analytes through} \\ \text{the sensor's semi permeable membranes} \end{pmatrix}$$

The x, y, z analyte concentrations are related to the equilibrated amperometric responses at a given interrogating potential through a function that involves signal contribution from interfering analytes and diffusion related processes. This diffusion related processes can be minimized by varying the $t_{bias}$ and/or $t_{wait}$ to attain steady state. The $t_{bias}$ and/or $t_{wait}$ at a given analyte concentration and at a given interrogating potential, can provide secondary measuring data for increasing reliability of the sensor. Such secondary measuring data can also provide the ability to estimate and accurately correct the natural decay of the sensor as a result of sensor drifts from changes in permeability of outer membranes and electrode-activity.

In an alternative methodology, the multi-potential interrogation can be performed together with the calibration sequences of FIGS. 4 and 5 to further increase the confidence level of assessing interferences while the sensor is operational in vivo.

In summary, the electro-active changes of the working electrode can be determined by comparing the differential values from two different internal calibration routines at two different analyte concentrations. In another embodiment, the electro-active changes of the said working electrode can be determined by comparing the time dependent decay of the amperometric signal immediately before and immediately after the time interval. In addition, the time-dependent decay involves determining the slope of the time-dependent decay curve. The slope of the time-dependent curves involves interrogating the sensor at two different $t_{bias}$ times. The slope of the time-dependent decay curve is obtained by comparing the signal value at the final and mid point of the curve.

The disclosed sensor along with the testing methodology disclosed herein has a number of advantages. The implantable glucose sensors can use periodically biased amperometry for interrogation to improve the sensor's sensitivity and linearity while at the same time enabling internal calibration against sensor drifts that originate from changes in either electrode activity or membrane permeability as a result of fouling, calcification and/or fibrosis.

The aforementioned features provide numerous advantages over other comparative biosensors in that they exhibit high linearity and sensitivity. They take into account the contribution of exogenous interfering species and provide internal calibration routines to control and reduce sensor-induced drift based on in vivo induced effects that change the permeability of semi-permeable membrane. These features also account for the gradual decay in electrode activity.

In addition, the implantable glucose sensor uses a hydrogel layer that comprises PVA alone. The use of PVA ensures a homogeneous coverage of the immobilized glucoseoxidase ($GO_x$) enzyme layer 110. It also facilitates the storage of $O_2$ and permits control of the amount of stored $O_2$ by varying the number of freeze-thaw cycles for the PVA.

The following examples, which are meant to be non-limiting were conducted to demonstrate the method of manufacturing the implantable glucose sensor disclosed herein. These examples also demonstrate some of the methods of interrogation and calibration of the implantable glucose sensor disclosed herein.

EXAMPLES

Example 1

This example was conducted to demonstrate the effect of the application of a biasing voltage to the surface of the working electrode of the glucose sensor. In order to increase the signal to noise ratio for a spectroscopic technique to successfully interrogate the effect of bias and presence of electro-active species, a thin layer of poly (ortho-phenylene diamine) (PPD) (which acts as the electrically conducting membrane 106) was electropolymerized on top of an indium tin oxide (ITO) coated substrate, a transparent conductor which can also be a material for working electrode.

Figure 8:
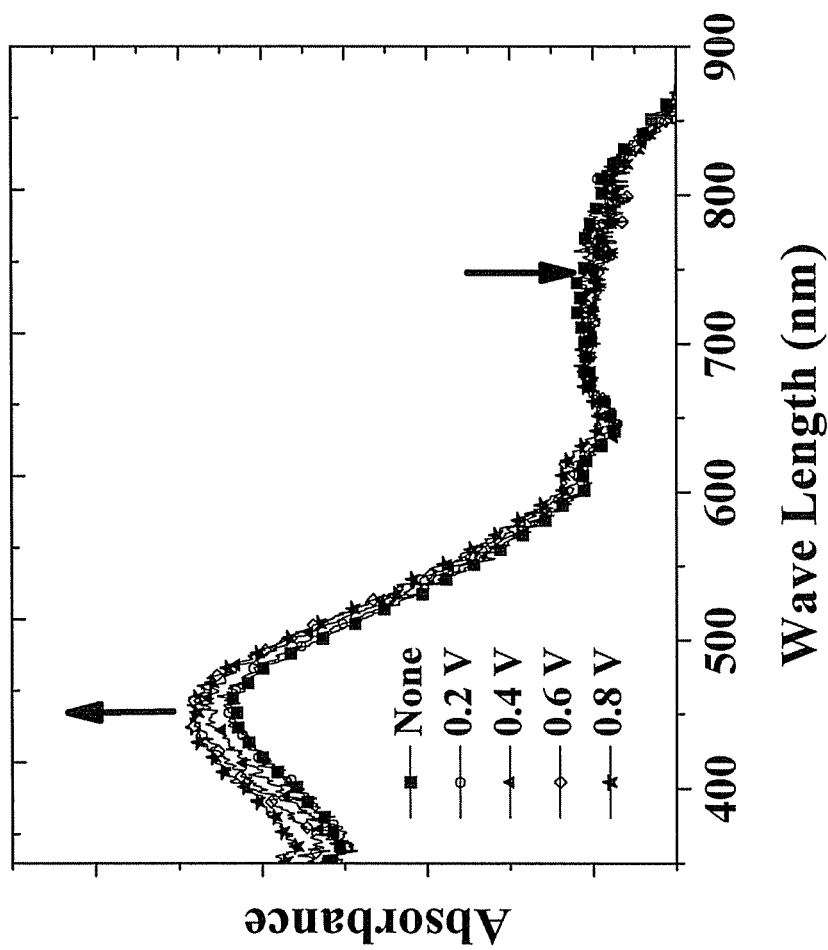
FIG. 8 is an ultraviolet-visible-near infrared (UV-Vis-NIR) absorption spectra of a poly(ortho-phenylene diamine) (PPD) film as a function of the applied biasing voltage.

The approximate thickness of the electropolymerized PPD film is ca. 10 nanometers (nm) and is comparable to that on an actual glucose sensor. FIG. 8 illustrates five overlapping UV-Vis-NIR absorption curves of the PPD films taken at different biasing voltages (0 Volts (V), 0.2V, 0.4V, 0.6V and 0.8V) with respect to a Ag/AgCl reference electrode. The application of the biasing voltage increases the intensity of the 450 nm absorption peak while decreasing the broad NIR absorption, with an isosbestic point ca. 690 nm. This indicates that PPD changes its conductivity with the application of higher bias.

Figure 9:
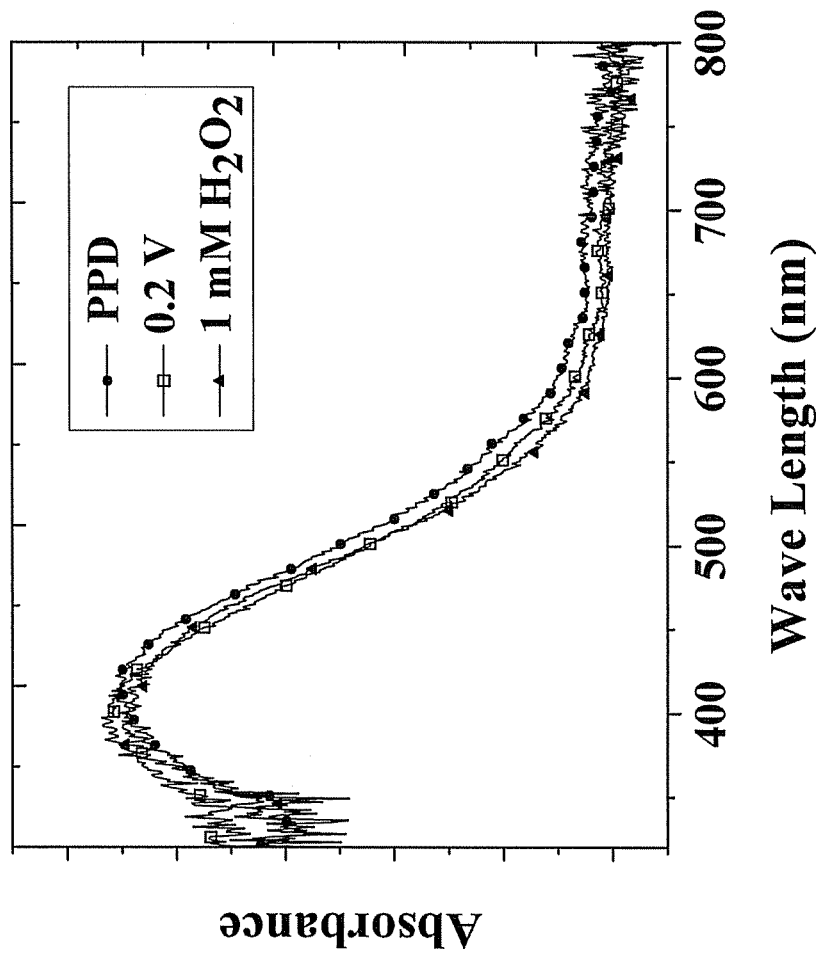
FIG. 9 is a UV-Vis absorption spectra of poly phenylene diamine (PPD) film, first biased for 150 sec at 0.2 V followed by removal of the biasing voltage and exposure to various concentration of $H_2O_2$.

FIG. 9 illustrates the UV-Vis-NIR absorption spectra for the same PPD film that was first biased for 150 sec at 0.2 V followed by removal of bias and exposure to 1 millimolar (mM) of $H_2O_2$. The spectra in the FIG. 9 shows that the application of a 0.2 V bias leads to a blue-shift in the 400 nm absorption range and decrease in broad NIR absorption corresponding to the changes in conductivity of PPD as shown in FIG. 8. Upon exposure to 1 mM $H_2O_2$, the 400 nm absorption range was red-shifted, thus opposing the action of the applied bias. This demonstrates that the generated $H_2O_2$ interferes with the oxidation state of PPD and therefore causes changes to the electrochemical activity of the working electrode.

These spectroscopic results are in agreement with the amperometric sensor behavior shown in FIG. 2, suggesting that the rapid sensitivity decrease might originate from over-oxidation of PPD that renders it less conductive and therefore less prone to receive electrons from the reaction 2 detailed above. Upon the removal of the positive bias, the $H_2O_2$ whose levels depend on the permeability of the semi permeable membrane(s), brings the electrode (i.e. PPD) to its conductive state.

Example 2

This example was conducted to demonstrate the different reactivities of the working electrode depending on whether the device is operated in a continuous or periodic biasing mode. The working electrode for this example is denoted by the nomenclature—Pt/PPD/$GO_x$/(HAs—$Fe^{3+}$)$_5$, where the electrode comprises platinum, the electrically conducting membrane comprises PPD, the enzyme layer comprises $GO_x$ and the semipermeable membrane comprises of a humic acid—$Fe^{3+}$ (HAs—$Fe^{3+}$)$_5$ layer.

Figure 10:
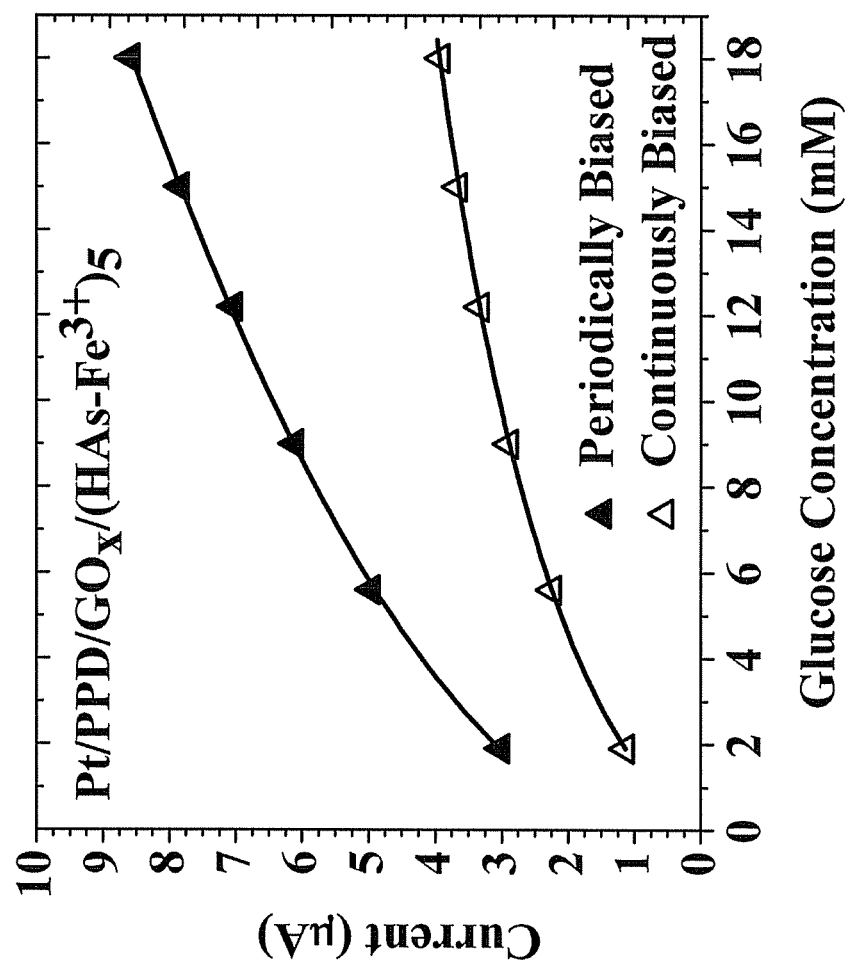
FIG. 10 is a graphical response vs. glucose concentration of a Pt/PPD/$GO_x$/(HAs—$Fe^{3+}$)$_5$ glucose working electrode vs. a Ag/AgCl reference electrode, when tested in continuous and periodically biased amperometry. The periodically biased amperometry is carried out at the initial stages of Regime A in FIG. 3.

FIG. 10 demonstrates the different reactivities of the working electrode when it is operated in continuous vs. periodic biasing at a $t_{bias}$=1 second. The biasing voltage was 0.7 V and the reference electrode comprises Ag/AgCl. For the periodic biasing mode, the operation took place in regime A (as witnessed in the FIG. 2), which explains its higher recorded amperometric current versus that for the continuous biasing mode that operates in regime B. As can be seen from the FIG. 10, one of the advantages of periodic biasing is that greater sensor linearity can be achieved because the pristine state and consequently pristine activity of the electrode is retained by virtue of subjecting it to periodic biasing.

Example 3

Figure 11:
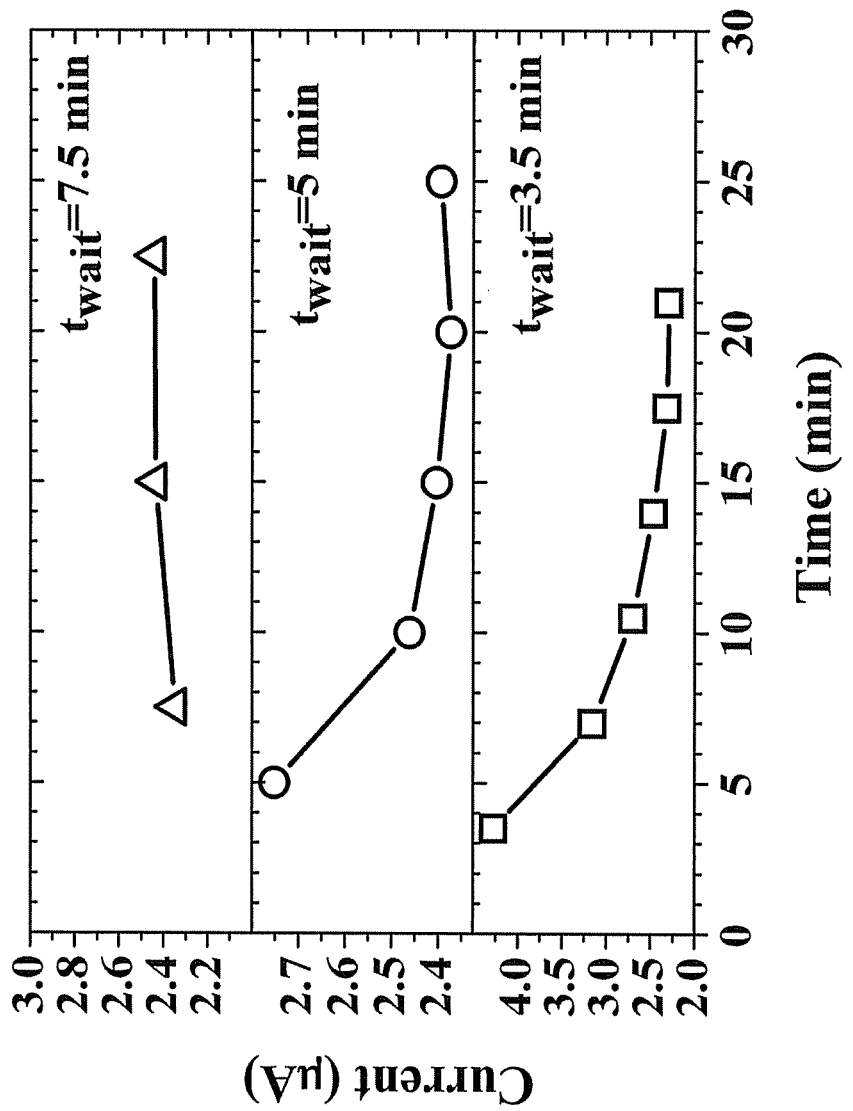
FIG. 11 is a graph depicting a 1-second periodic-biased amperometric response as a function of $t_{wait}$ for a Pt/PPD/$GO_x$/(HAs—$Fe^{3+}$)$_5$ working electrode operated at 0.7 V vs. a Ag/AgCl reference electrode on a constant glucose concentration of 2 mM.

This example was conducted to demonstrate the conditions for equilibrium performance of the working electrode. The working electrode used in this example has the same configuration as that described in the Example 2. FIG. 11 illustrates the periodic biasing operation of the device at a constant glucose concentration of 2 mM when operated at a biasing voltage of 0.7 V. The reference electrode comprised Ag/AgCl. The biasing time $t_{bias}$ was of 1 second duration and the waiting time $t_{wait}$ was varied from 3.5 to 5 to 7.5 minutes.

This device operates in regime A (see FIG. 2) where sensor equilibration has not been attained. The sensor has been removed from the test cell, washed with deionized (DI) water and reconnected to the electrochemical potentiostat prior to commencing the next set of $t_{wait}$ experiments. Amperometric response stabilization is witnessed at 7.5 min. This indicates that the departure from equilibrium by the application of a biasing time ($t_{bias}$) of 1 second requires approximately 7.5 minutes of incubation in a $H_2O_2$ environment generated by 2 mM of glucose.

Example 4

This example was conducted to demonstrate the advantages provided by the use of a hydrogel layer that comprises only PVA. This example compares the response of two electrodes—one that contains PVA while the other does not contain the PVA.

As noted in the FIG. 1, a first layer of a first hydrogel 118 is disposed between the semi-permeable membrane 114 and a second layer of the second hydrogel 122. In this example, the semi-permeable membrane 114 comprises an LBL-grown membrane while the second layer of the second hydrogel 122 comprises TRM-containing micro spheres.

In general, water-containing hydrogels act as poor absorbers for oxygen as opposed to hydrophobic polymers. It is therefore desirable to incorporate hydrophobic domains within the hydrogels to increase their oxygen storing ability.

Figure 12:
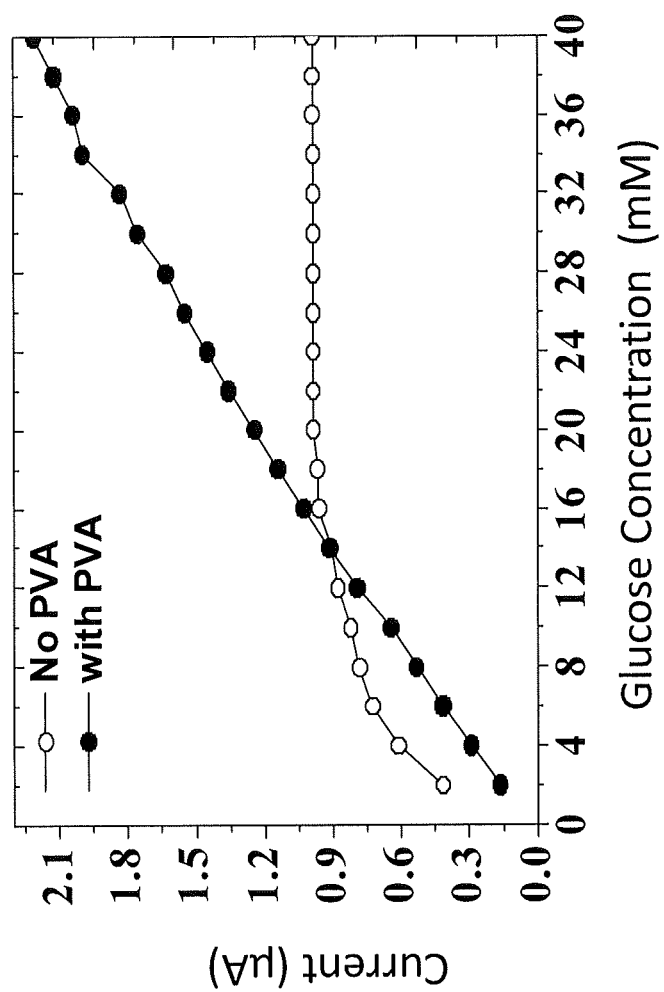
FIG. 12 is a graph depicting a continuous biased amperometric response of a Pt/PPD/$GO_x$/(HAs—$Fe^{3+}$)$_5$ working electrode, biased at 0.7 V vs. a Ag/AgCl reference electrode, in the presence and absence of top PVA layer that has been subjected to three freeze-thaw cycles.

FIG. 12 shows the amperometric response for a continuous biasing voltage of 0.7 V when used on two working electrodes. Both electrodes are similar to that used in the Example 3, except that one has no PVA, while the other has a layer of PVA hydrogel. Thus in terms of the nomenclature adopted in the Example 2, one electrode comprises Pt/PPD/$GO_x$/(HAs—$Fe^{3+}$)$_5$ (with no PVA) while the other comprises Pt/PPD/$GO_x$/(HAs—$Fe^{3+}$)$_5$/PVA (with PVA). The amperometric response is measured versus a Ag/AgCl reference electrode for varying glucose concentrations. As can be seen in the FIG. 12, the incorporation of PVA dramatically increases linearity and sensor sensitivity when compared to the device that does not contain PVA.

Figure 13:
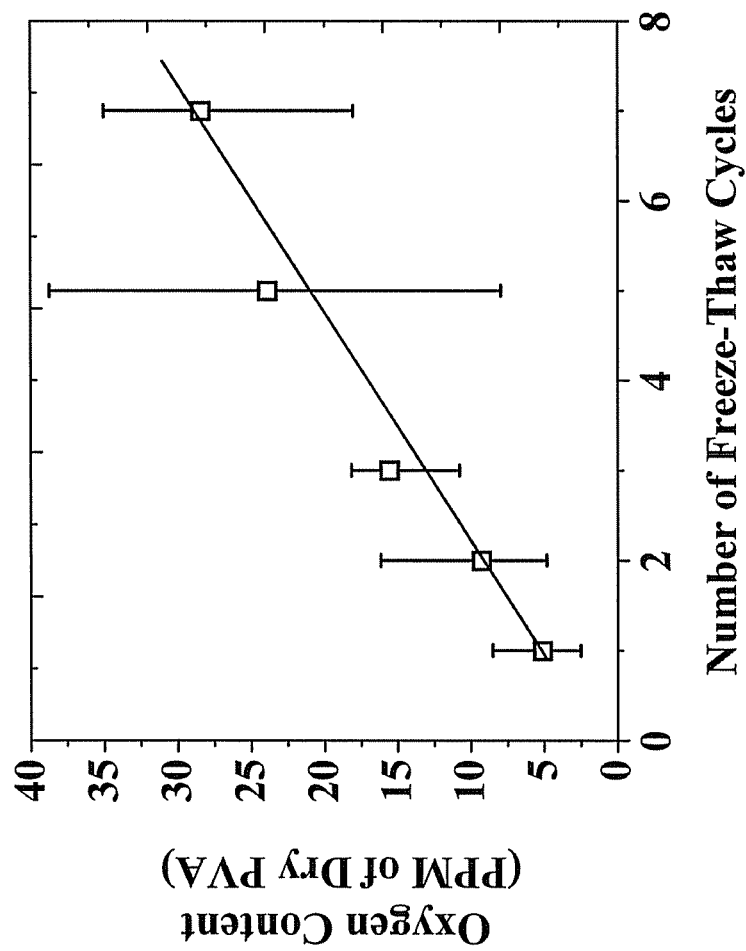
FIG. 13 is graph depicting a variation of PVA-stored $O_2$ content as a function of the number of freeze thaw cycles.

In order to investigate the role of PVA in enhancing sensor's linearity and sensitivity, the oxygen content in the PVA layer was determined. These were determined by sealing a known amount of a PVA sample in a glass tube under vacuum (hereinafter "tube containing PVA" sample). This was achieved by filling the actual tube with a 10% weight per unit volume of aqueous PVA solution and performing a number of freeze-thaw cycles varying from 1 to 7 prior to flame sealing the tube under vacuum, while the gel is frozen. This hydrogel containing glass capsule was then taken into an air tight chamber containing 50 ml amount of DI water and a commercial oxygen sensor. Following this, a test cell was sealed from the atmosphere and $N_2$ was bubbled in order to decrease the oxygen concentration in the test cell. When the oxygen concentration in the test cell reached 0 μM, the tube containing PVA was crushed, to let its oxygen level equilibrate with the surrounding media. The increase in the oxygen level was recorded as function of the number of freeze-thaw cycles, and the experiment was repeated in triplicate. As shown in FIG. 13, the oxygen content of PVA increases with increasing freeze-thaw cycles, which indicates that the nature of the linearity and sensitivity increase in FIG. 12, originates from the ability of PVA to store oxygen. This relationship between the number of freeze thaw cycles and the amount of stored oxygen was hitherto unknown.

Example 5

This example was conducted to demonstrate the effect of incorporating carbon nanotubes in the PPD layer (see layer 106 of FIG. 1). To enhance the ability of the present glucose sensor to also detect oxygen, the PPD layer was formed (through electropolymerization) in the presence of acid treated single walled carbon nanotubes (SWNTs). The incorporation of SWNTs in PPD is believed to originate from charge balancing the positively charged PPD.

Figure 14:
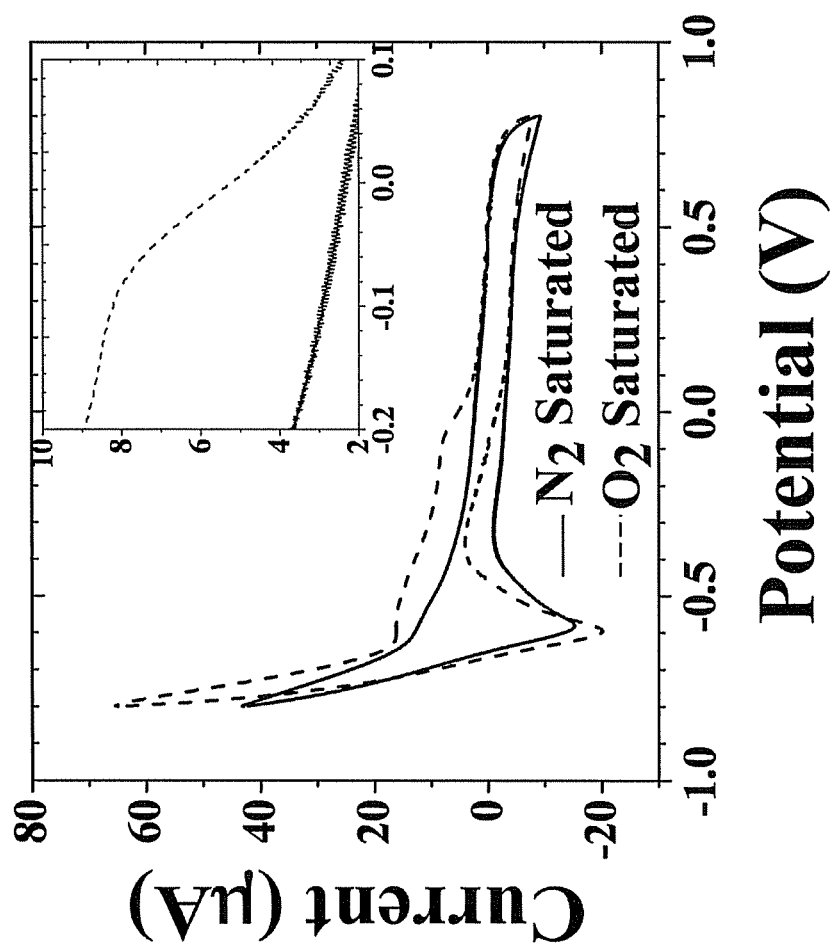
FIG. 14 is a cyclic voltammogram of a Pt/PPD+SWNT working electrode versus a Ag/AgCl reference electrode in PBS buffer solution that has been saturated with either air (i.e. O2) (dashed line) or $N_2$ (solid line). For purpose of clarity, the inset shows a blowup of the results in the 0.1 to −0.2 Volt region.
Figure 15:
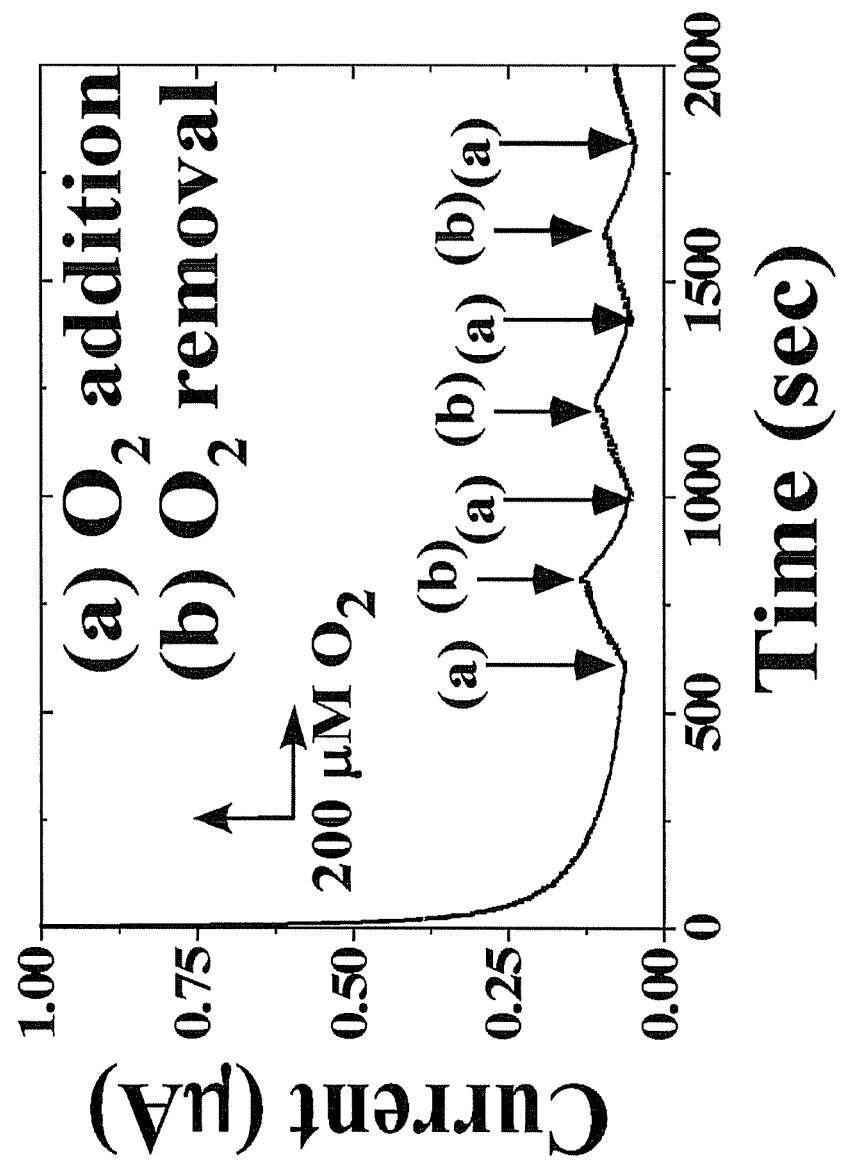
FIG. 15 is graph depicting a continuously biased amperometric response of a Pt/PPD+SWNT working electrode, biased at −0.1 V versus a Ag/AgCl reference for three successive cycles of addition and removal of $O_2$.

FIG. 14, illustrates the cyclic voltammogram of the Pt/PPD+SWNT device in a 0.1 M Phosphate Buffer Saline (PBS) buffer solution (pH=7.2) with and without the presence of $O_2$. The reference electrode is Ag/AgCl. In the presence of the SWNTs, a shoulder at −0.1 V can be seen. This shoulder corresponds to the reduction of oxygen, which is electrocatalyzed by the combination of PPD and SWNTs. The corresponding continuously biased amperometric response of the same device operated at −0.1 V vs. the Ag/AgCl reference is shown in FIG. 15. As can be seen, the device responds quickly and reproducibly to changes in oxygen concentration.

Example 6

Figure 16:
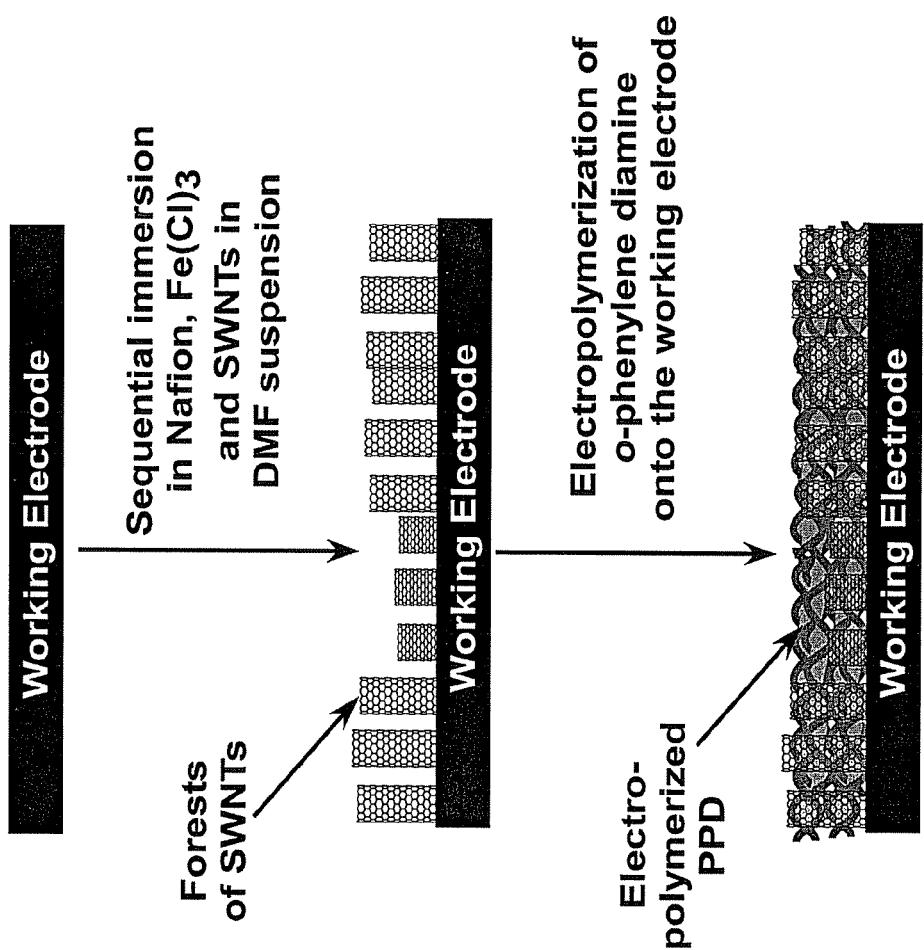
FIG. 16 is a schematic representation of the process used to modify a surface of a working electrode with a composite containing a network of SWNTs intercalated with a layer of an electropolymerized conducting polymer.

This example demonstrates a strategy to enable simultaneously the "direct wiring" of the redox enzyme to the working electrode (as in third generation biosensors) via SWNT networks while at the same time utilizing the enhanced electrocatalytic activity of PPD/SWNT composites to enable oxygen sensing. As shown in FIG. 16, the working electrode is decorated with SWNT networks via sequential immersion first in NAFION®, second in an aqueous solution of $FeCl_3$ and third in acid treated SWNTs that have been washed and dispersed in N,N-dimethylformamide (DMF). These carboxy-functionalized tips of the SWNT network can be covalently reacted with either a variety of redox enzymes (i.e., $GO_x$) or with its Flavin Adenine Dinucleotide (FAD) cofactor followed by reconstitution with the apo-enzyme (i.e., apo-$GO_x$). Subsequently the PPD can be grown within this SWNT network via electropolymerization of OPD to PPD as shown in FIG. 16.

As can be seen in the aforementioned examples, the use of a PVA hydrogel layer facilitates the storage of $O_2$ and permits control of the amount of stored $O_2$ by varying the number of freeze-thaw cycles for the PVA. The use of the PVA hydrogel layer in the sensor when used in conjunction with intermittent biasing permits the sensor to be self-calibrating which reduces maintenance costs and replacements costs.

While the invention has been described in detail in connection with a number of embodiments, the invention is not limited to such disclosed embodiments. Rather, the invention can be modified to incorporate any number of variations, alterations, substitutions or equivalent arrangements not heretofore described, but which are commensurate with the scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method comprising:
performing periodic biasing amperometry on a sensor, the sensor comprising:
a reference electrode;
a counter electrode;
a working electrode; the working electrode being disposed in the vicinity of the reference and counter electrode;
an electrically conducting membrane; the electrically conducting membrane being in operative communication with the working electrode;
an enzyme layer; the enzyme layer being in operative communication with the working electrode;
a semi-permeable membrane; the semi-permeable membrane being in operative communication with the working electrode introducing a sample comprising an analyte being measured to the sensor;
the periodic biasing amperometry comprising:
determining a normal operating state for the sensor by biasing the working electrode for the same duration of time at intervals ($t_{wait}$) having the same periods of time at a number of testing potentials;
repeating the periodic biasing for all the testing potentials;
continuing the periodic biasing until a steady state is attained for all the testing potentials;
conducting an internal calibration of the sensor after the analyte being measured has reached a steady state; the internal calibration comprising a time interval ($t_{cal}$) where the periodic biasing is not applied; where $t_{cal}$=n× $t_{wait}$, where n is a number of about 2 to about 10;
measuring a periodic biasing amperometric signal difference immediately before and immediately after the time interval ($t_{cal}$);
comparing the differential with a calibration chart to obtain sensitivity factors; and
applying the sensitivity factors to the sensor to correct against drifts; and
performing biasing amperometry at a time interval of $t_{eq}$ to ensure that the sensor returns to its normal operating state; where $t_{eq}$ is less than $t_{wait}$.

2. The method of claim 1, where the sensitivity factors are applied to gradually prorate recorded values obtained from the sensor.

3. The method of claim 1, where the drifts originate from changes in electro-activity of the working electrode.

4. The method of claim 3, wherein the changes in electro-activity of the working electrode are determined by comparing signal differentials from two different internal calibration routines at two different analyte concentrations.

5. The method of claim 3, wherein the changes in electro-activity of the working electrode are determined by comparing the time dependent decay of the amperometric signal immediately before and immediately after the time interval $t_{cal}$.

6. The method of claim 5, wherein the time-dependent decay involves determining a slope of a time-dependent decay curve.

7. The method of claim 5, wherein the slope of the time-dependent curve is determined by interrogating the sensor at two different biasing time intervals.

8. The method of claim 5, where the slope of the time-dependent decay curve is obtained by comparing at a signal value at a mid-point and a final of the curve.

* * * * *